United States Patent [19]

Theresia Meeusen et al.

[11] Patent Number: 5,650,154
[45] Date of Patent: Jul. 22, 1997

[54] PROTECTIVE ANTIGENS AGAINST DISEASE PATHOGENS

[76] Inventors: Elza Nicole Theresia Meeusen, 17 Wolseley Parade, Kensington, Victoria 3550; Malcolm Roy Brandon, 14 Castella Street, Ivanhoe, Victoria 3079; Vernon Morrison Bowles, 3/30 Hunter Street, Malvern, Victoria 3144; John Walker, 26 Clapham Street, Balwyn, Victoria 3103; Mark Douglas Gorrell, 56A View Street, Annandale, New South Wales 2038, all of Australia

[21] Appl. No.: 314,172

[22] Filed: Sep. 28, 1994

Related U.S. Application Data

[63] Continuation-in-part of Ser. No. 70,632, Jun. 1, 1993, abandoned, which is a continuation of Ser. No. 470,908, Jan. 26, 1990, abandoned.

[30] Foreign Application Priority Data

Feb. 1, 1989 [AU] Australia .................. PJ2504
Feb. 1, 1989 [AU] Australia .................. PJ2505

[51] Int. Cl.⁶ .............. A61K 39/002; A61K 39/05
[52] U.S. Cl. .................. 424/265.1; 424/245.1; 424/266.1; 530/350; 530/412
[58] Field of Search ............. 424/245.1, 265.1, 424/266.1; 530/350, 412, 822

[56] References Cited

U.S. PATENT DOCUMENTS 3,853,990 12/1974 Madigan et al. .......... 424/87
4,743,446 5/1988 Bennett .................. 424/85

FOREIGN PATENT DOCUMENTS

49035/90 11/1990 Australia .

OTHER PUBLICATIONS

Roitt, et al., *Immunology*, Gower Medical Publishing, pp. 8.1–8.2 and p. 25.7 (1985).

*Primary Examiner*—James C. Housel
*Assistant Examiner*—Rodney P. Swartz
*Attorney, Agent, or Firm*—Merchant, Gould, Smith, Edell, Welter & Schmidt

[57] ABSTRACT

Methods and kits for identifying antigens from a pathogen. The antigens identified are preferably those that provide protection for an animal against the pathogen. The steps of the method include providing a sample of the pathogen, isolating the protective antigen from the sample of antigen with an antibody probe. The antibody probe is produced by obtaining a biological sample containing antibody producing cells from an immune animal infected with or challenged by the pathogen or pathogen extract, and obtaining the antibodies from these cells by culturing the cells. These methods and kits are useful for preparing antigens to be used as vaccines, in diagnostic kits, and to prepare polyclonal or monoclonal antibodies.

5 Claims, 19 Drawing Sheets

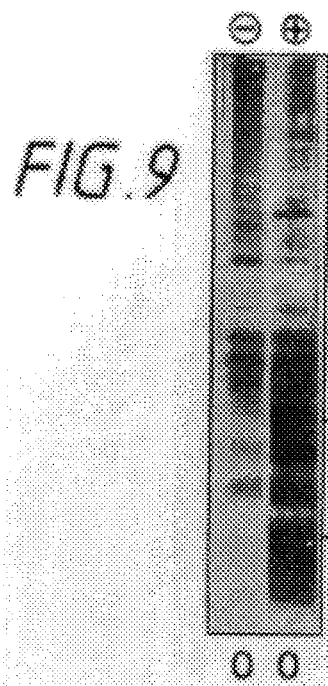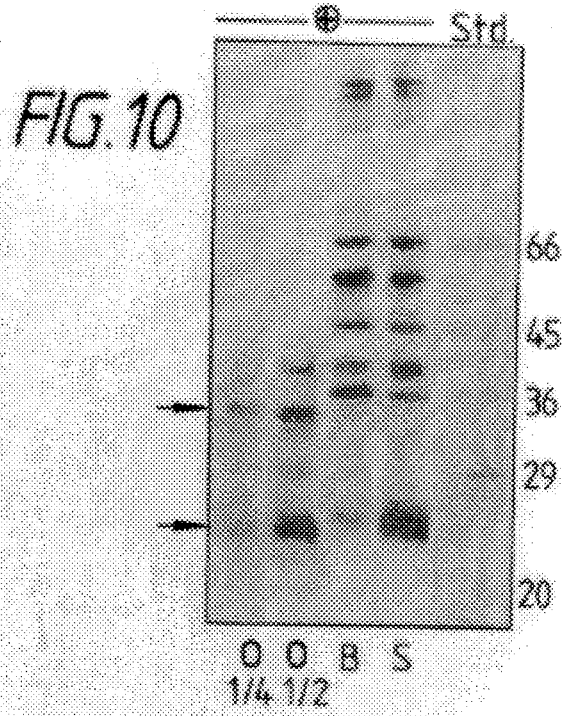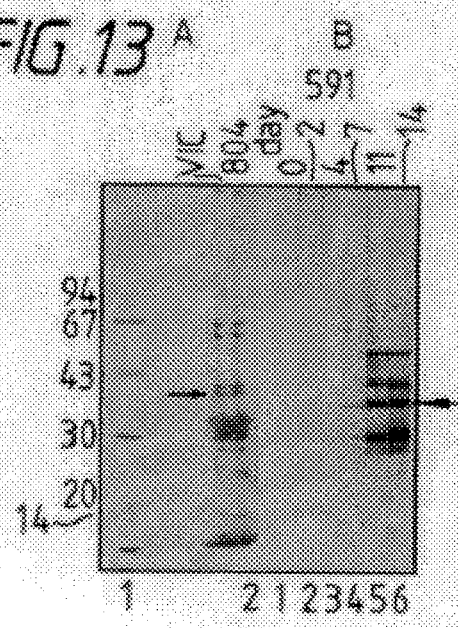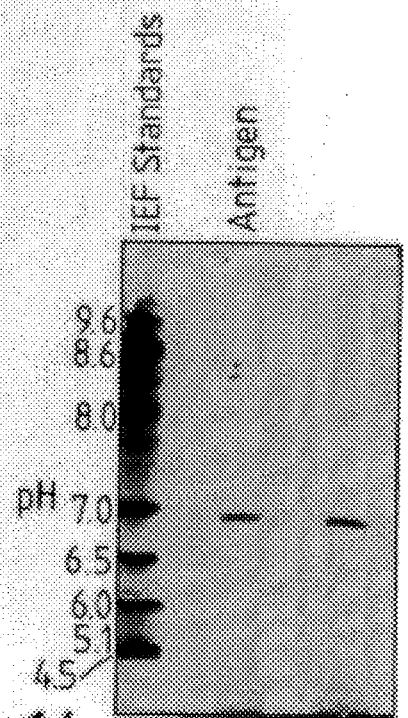

Days Post Challenge

FIG. 22A

```
CTGGCACAGTGACCCAAGGATAAATTTGAGAGTTTTCACACGGGTGGGATACGCAAACCTTGACCGTCCCCACCA    75
TCCCAAAACCTTGTATATATGTGACACAAATACTTAAATTTATATAACTTTTCACTTGCCCAAGGAATTAAAATG    150
```

```
                                                    M  H  N  S  P  R  S
CAGTCTTAAGATAGGACTTACTTCTTAACGATGTCTTATTGAAGGGGCAGGCACATGCATAATTCTCCTCGATCA    225

V  S  R  L  I  T  V  G  I  T  S  A  L  F  A  S  T  F  S  A  V  A  S  A  E
GTCTCACGCCTTATTACGGTAGGCATAACTTCCGCTCTCTTTGCTAGCACTTTTAGCGCTGTAGCATCCGCAGAG   300

S  A  T  L  S  K  E  P  L  K  A  S  P  G  R  A  D  T  V  G  V  Q  T  T
TCTGCAACCTTGTCCAAAGAGCCGCTGAAAGCAAGCCCTGGACGCGCAGACACGGTGGGAGTGCAAACAACATGT   375

N  A  K  P  I  F  F  G  Y  Y  R  T  W  R  D  K  A  I  Q  L  K  D  D  D  P
AACGCCAAACCAATTTTCTTCGGCTATTACCGCACCTGGCGCGATAAGGCCATCCAGCTTAAGGACGACGACCCT   450

W  K  D  K  L  Q  V  K  L  T  D  I  P  E  H  V  N  M  V  S  L  F  H  V  E
TGGAAAGACAAGCTCCAGGTCAAGCTGACGGACATTCCCGAGCACGTCAATATGGTCTCGTTGTTCCATGTGGAA   525

D  N  Q  K  S  D  Q  Q  F  W  E  T  F  H  R  E  Y  Q  P  E  L  K  K  R  G
GATAATCAGAAGAGCGATCAGCAATTCTGGGAAACCTTCCACAGGGAATACCAGCCCGAGCTCAAAAAACGCGGT   600

T  R  V  V  R  T  V  G  A  Q  L  L  L  N  K  I  K  D  K  N  L  Y  G  K  H
ACCCGAGTTGTTCGGACCGTCGGCGCGCAGTTGCTGCTCAATAAGATTAAAGATAAAAACCTCTACGGAAAGCAT   675

V  E  D  D  Y  K  Y  R  E  I  A  R  D  V  Y  N  E  Y  V  V  K  H  N  L  D
GTTGAAGACGACTACAAGTATCGGGAGATAGCACGCGATGTATATAACGAGTACGTCGTCAAACATAATCTTGAT   750
```

FIG. 22B

```
          V  E  D  D  Y  K  Y  R  E  I  A  R  D  V  Y  N  E  Y  V  V  K  H  N  L  D
     GTTGAAGACGACTACAAGTATCGGGAGATAGCACGCGATGTATATAACGAGTACGTCGTCAAACATAATCTTGAT   750

G  L  D  V  D  M  E  L  R  Q  V  E  K  Q  L  N  L  K  W  Q  L  R  K  I  M
     GGCTTAGACGTAGACATGGAACTCCGCCAGGTGGAGAAACAACTAAACCTCAAGTGGCAGCTGCGCAAAATCATG   825
                                        ─────────────────────────────────────

G  A  F  S  E  L  M  G  P  K  A  P  A  N  E  G  K  K  P  D  H  E  G  Y  K
     GGAGCGTTCTCCGAGCTCATGGGCCCCAAAGCCCCTGCAAATGAGGGGAAAAAGCCAGATCATGAGGGTTATAAG   900

Y  L  I  Y  D  T  F  D  N  A  Q  T  S  Q  V  G  L  V  A  D  L  V  D  Y  V
     TACCTTATTTATGACACCTTTGATAATGCCCAGACATCACAGGTCGGGCTGGTCGCAGACCTAGTGGATTATGTC   975

L  A  Q  T  Y  K  K  D  T  K  E  S  V  T  Q  V  W  N  G  F  R  D  K  I  N
     CTGGCTCAGACCTATAAGAAGGACACAAAAGAGAGCGTCACCCAGGTATGGAATGGCTTCCGAGACAAGATCAAT  1050

S Ⓒ  Q  F  M  A  G  Y  A  H  P  E  E  N  D  T  N  R  F  L  T  A  V  G  E
     TCCTGCCAGTTTATGGCTGGGTATGCCCACCCGGAGGAAAATGACACAAATCGATTCCTCACCGCAGTAGGAGAA  1125

V  N  K  S  G  A  M  Q  V  A  E  W  K  P  E  G  G  E  K  G  G  T  F  A  Y
     GTGAATAAATCTGGCGCAATGCAGGTCGCAGAGTGGAAGCCAGAAGGCGGAGAAAAGGGCGGGACCTTCGCCTAC  1200

A  L  D  R  D  G  R  T  Y  D  G  D  D  F  T  T  L  K  P  T  D  F  A  F  T
     GCCCTGGATAGGGACGGGCGCACCTACGATGGAGACGATTTCACCACACTCAAACCGACCGATTTTGCCTTTACC  1275

K  R  A  I  E  L  T  T  G  E  S  S  T  D  L  G  K  P  T  G  S  R ...
     AAGCGCGCAATCGAGCTAACCACCGGCGAATCGTCTACAGACTTAGGAAAGCCAACTGGTTCTAGATAAACGAGT  1350

AGTTTTCCTTTCACAATTCCTAATAAGTCCCAACACCTAGAGGAGGACTCTATAGCAAATAACAAAAATAATCTC  1425

ACGGGCCGCATAACACAAGGCCCACCA                                                   1552
```

PROTECTIVE ANTIGENS AGAINST DISEASE PATHOGENS

CROSS REFERENCE TO RELATED APPLICATION

This application is a continuation-in-part of U.S. patent application Ser. No. 08/070,632, filed Jun. 1, 1993, now abandoned, which is a continuation of U.S. Ser. No. 07/470,908 filed Jan. 26, 1990, now abandoned.

The present invention relates to antibody probes and the use of such probes in a process for detection and purification of a number of protective and diagnostic antigens, the preparation thereof and their use in the formation of vaccine compositions.

Considerable effort has been devoted in the prior art to the development of vaccines to control parasitic, bacterial and other infections of animals including livestock. However, little progress has been achieved to this end in the past 5 years although the associated technology of producing foreign products in large amounts in eukaryotic and prokaryotic organisms has advanced enormously. The identification of protective antigens in important pathogenic infections in animals, for example, has remained the principal stumbling block to the generation of vaccines.

One of the principal reasons for this is the enormous complexity of, for example, parasitic organisms which may have up to 10% of the genetic information of a mammal, and as a consequence have the ability to produce an enormous array of products at various stages of their life cycle, only a few of which may be important in developing an effective vaccine. In most instances, the researcher is confronted by hundreds of potential antigens. The central puzzle still remaining is which are the parasite antigens that elicit host-protective immune responses. The cloning of a parasite antigen chosen on the basis of hope or inspiration, at considerable difficulty, expense and time, in theory may result in the development of an effective vaccine. However, in most instances, this approach has resulted in failure.

In the prior art in parasitic infections the emphasis has been placed on the screening of crude parasite antigen mixtures, parasite cDNA or genomic libraries with whole serum antibodies used as "probes". Serum contains large numbers of antibodies against other pathogens and antigens. In addition, most antibodies against the parasite are directed against non-protective antigens.

Very little effort has been made to improve the antibody probes used to screen crude parasitic antigen mixtures or parasite cDNA libraries, although this is vital for the detection of protective antigens and the monitoring of protective epitopes of these antigens during their subsequent molecular cloning.

For example, *Haemonchus contortus* is an intestinal parasite of sheep that localizes in the abomasum (fourth stomach). Late larval and adult stages of the parasite feed on whole blood. The parasite is responsible for sizeable economic loss to the sheep industry in Australia and considerable loss overseas as it is a potentially fatal disease. Despite these losses no successful vaccine has been developed in the prior art against this parasite.

*Caseous lymphadenitis* (abbrev. CLA, also called Cheesy Gland) is a chronic infection of sheep and goats that is caused by the bacterium *Corynebacterium pseudotuberculosis* (syn. *C. ovis*). A complex cell-free vaccine for CLA (GLANVAC, Commonwealth Serum Laboratories) is known in the prior art and is currently administered either alone or as part of a 6 component antibacterial vaccine (6 in 1). The protection afforded by this vaccine is attributed to the inactivated toxin (i.e. toxoid) component. The toxin has a relative molecular weight of approximately 31 k daltons when run on 12.5% SDS-PAGE under reducing conditions. Whilst this prior art vaccine does generate some protective effect, the vaccine is complex and expensive, and significant numbers of infections may still occur.

*Fasciola hepatica* (liver fluke) is a parasitic infection which develops in the liver and bile ducts in sheep and cattle. Liver fluke may cause chronic and acute losses in sheep and cattle industry. Numerous prophylactic and therapeutic treatments are known in the prior art but their effects have proved limited and liver fluke remains a chronic veterinary disease.

*Taenia hydatigena* is a parasitic infection which also develops in the liver of sheep. It is transferred from animal to animal by infected dogs and may generate some losses in the sheep industry. No successful vaccine has been developed in the prior art against this parasite.

It is accordingly an object of the present invention to overcome, or at least alleviate, one or more of the difficulties related to the prior art.

Accordingly, in a first aspect, the present invention provides a method for producing at least one antibody against a pathogen, which method includes providing a biological sample from an animal infected with, or challenged by, the pathogen or pathogen extracts;

isolating cells from biological sample;

culturing the cells in vitro in a suitable culture medium; and harvesting antibodies produced from said cells.

The animal from which the biological sample may be taken may be of any suitable type. The animal from which the biological sample is taken may be an immune animal. The biological sample may be taken a short time after the immune animal has been challenged with a pathogenic infection. The animal may be a mammal including humans. The mammal may be a domestic animal such as sheep or cattle.

In the following description, reference will be made to a method of identifying parasitic and bacterial immunogens important in diseases of sheep and cattle more specifically to the parasitic infections *Taenia hydatigena* (cestode), *Haemonchus contortus* (nematode), *Fasciola hepatica* (trematode) and the bacterial pathogen *Corynebacterium pseudotuberculosis*. It should be understood, however, that such immunogens and pathogens are illustrative only and the method is generally applicable to animals including humans. In particular, the method described herein may be used to detect the immunogen in auto-immune diseases.

The biological animal sample may be of any suitable type. The biological sample may be from animal tissues, organs, blood, lymph or lymph nodes. The biological sample may be taken from any section of the infected animal. However, it is preferred that the samples be taken from the infected site or an area of a lesion which may be formed in certain diseases or an area close to the infected site or a lesion such as in the lymph nodes.

However, serum/plasma samples are not preferred as the biological samples according to this aspect of the present invention. It has been found that the majority of antibodies found in a serum/plasma sample are irrelevant to protection or specific diagnosis of a pathogen or are unrelated to the pathogen. In addition, other serum/plasma components may interfere with the specific reactions between pathogen components and antibodies to them.

In contrast, the probes described in the present invention are highly enriched in pathogen-specific antibodies and can be selected to be restricted to the pathogen-stage of particular importance to protective immunity.

It is preferred that the biological samples are taken from the animals at a predetermined time in the development of a disease. In general, for a parasitic infection, it has been found that the biological samples should be taken a short time after an infection with a pathogen or after injection with products obtained from a pathogen. It is postulated that a parasite is vulnerable for only a short time after entering the subject after which it changes structure and is no longer vulnerable to immune attack and may no longer induce protective antibodies.

The cells isolated from the biological sample may include B cells. The cells may be isolated similarly at a time known to include a secretion and/or antibody producing period. Alternatively, the cells may include memory cells which may be generated at a later stage in certain diseases.

Thus, preferably the cells are taken a short time after in vivo stimulation, preferably within approximately 2 to 13 days thereafter with, for example, the relevant parasite stage thereby resulting in the in vivo induction of antibody forming cells which will secrete specific antibodies into the culture medium after in vitro incubation. No, or very few antibodies may be secreted in culture medium without prior in vivo stimulation of resting lymphocytes.

In vitro secretion of antibodies in the culture medium by recently activated B cells may be enhanced by the addition of helper factors to the cultures. The helper factors may be cytokines used along or in combination, including interleukin 1, 2, 3, 4, 5, 6, 7 and 8, colony stimulating factors, interferons and any other factors that may be shown to have an enhancing effect on specific B cell secretion.

The method of producing an antibody according to this aspect of the present invention may include a further step of activating the cells isolated to proliferate and secrete and/or release antibodies.

The cell activation step may include adding a cell activating agent to the culture medium. The cell activating agent may be parasite-derived or may be selected from mitogens and helper factors produced by leukocytes, or their synthetic equivalents or combinations thereof.

The mitogens may be selected from products derived from pokeweed (*Phytolacca americana*) also known as pokeweed mitogen (PWM), polyvinylpyrrolidone (PVP), polyadenylic-polyuridylic acid (poly(A-U)), purified protein derivate (PPD), polyinosinic-polycytidilic acid (poly(I-C), lipopolysaccharide (LPS), staphylococcal organisms or products thereof, Bacto-streptolysin O reagent (SLO), Staphylococcal phage lysate (SPL), Epstein-Barr virus (EBV), Nocardia water-soluble mitogen (NWEM), phytohemagglutinin (PHA) Concanavalin A (Con A) and dextran-sulphate and mixtures thereof. The cell proliferation agent may be any agent that indirectly or directly results in B cell proliferation and/or antibody secretion such as solid-phase anti-immunoglobulin. The helper factors may be cytokines including interleukin 1, 2, 3, 4, 5, 6, 7, and 8, colony stimulating factors, interferons and any other helper factors that may be shown when added alone, or in combination with other factors and agents to have an enhancing effect on specific B cell proliferation and/or antibody secretion. This in no way is meant to be an exhaustive list of mitogens and cell actuating agents including helper factors.

The in vitro culturing of the cells may be conducted with or without prior steps to separate sub-populations of cells. The harvesting of antibodies may be conducted by harvesting of the supernatant from the culture medium. This supernatant contains antibodies secreted by these cells during the in vitro culture or artificially released from the B cells, for example by lysis of the B cells. It has been found, surprisingly, that the antibody-containing supernatants may be used directly to detect antigens of a pathogen.

Accordingly, in a further aspect of the present invention there is provided a method for preparing an antigen associated with a disease pathogen, which method includes providing a sample of a disease pathogen; and an antibody probe including at least one antibody against
a disease pathogen produced by a method including
providing a biological sample from an animal infected with, or challenged by, the pathogen or pathogen extract;

isolating cells from the biological sample;

culturing cells in vitro in a suitable culture medium; and harvesting antibodies produced from said cells, probing the pathogen sample to detect at least one antigen with the antibody probe; and isolating the antigen detected.

The disease pathogen may be of any suitable type. The disease pathogen may be derived from any infectious agents including viruses, chlamydias, rickettsias, mycoplasmas, bacteria, spirochetes, fungi, protozoa, helminths (trematodes, nematodes, cestodes) and ectoparasitic arthropods (e.g. ticks, mites, blowflies) or may be an autoantigen or tumour antigen.

The disease pathogen is preferably a parasite, parasite extract or parasitic section thereof. The disease pathogen may be selected from *Haemonchus contortus*, an intestinal parasite of sheep, *Fasciola hepatica* (liver fluke) a parasitic infection which develops in the liver and bile ducts in sheep and cattle, or *Taenia hydatigena* a parasitic infection which also develops in the liver of sheep. Other parasites include *Lucilia cuprina*, Trichostrongylus spp, Boophilus spp, Ostertagia spp, Schistosome spp, Taenia spp and Echinococcus spp. However, the invention is not restricted thereto and the description following is merely illustrated by reference to these parasites.

In an alternative aspect, the pathogen sample may be taken from a bacterium. For example, the bacterium *Corynebacterium pseudotuberculosis* may be used.

In a preferred aspect, there is provided a method for preparing an antigen associated with a disease pathogen which method includes providing a sample of a disease pathogen taken from a disease pathogen at a stage of development during which it is though to be most susceptible to attack; and an antibody probe including at least one antibody against
a disease pathogen produced by a method including
providing a biological sample from an immune animal taken a short time after the immune animal has been challenged with a pathogenic or pathogen extract;

isolating cells from the biological sample;

culturing cells in vitro in a suitable culture medium; and harvesting antibodies produced from said cells.

The disease pathogen from which a sample may be taken may be at a stage of development of the pathogen during which it is thought to be most susceptible to attack. For example, for a parasitic cestode infection, it may be suitable to take the sample from the oncosphere stage. It has been found that antigens present in the oncosphere stage of a parasitic infection are not present, for example, in the metacestode stage. For a parasitic worm infection, it may be suitable to take the sample from the larval, preferably late larval stage. For a parasitic fluke infection, it may be suitable to take the sample from the juvenile fluke stage. A pathogen extract or preparation can be obtained from a disease pathogen using standard methods. The pathogen extract preferably includes one or more antigens of the pathogen.

The sample of disease pathogen may be mixed with a standard buffer solution and placed on a standard support such as an SDS-polyacrylamide gel to separate the proteins contained therein. The separated proteins may then be transferred to nitro-cellulose, nylon or other sheets.

The probing with a suitable antibody may further include subjecting the product produced thereby to a detection assay. The detection assay may include western blot techniques. The detection assay may be an immunoprecipitation assay, a radioimmunoassay, an enzyme-linked immunoassay or immunofluorescent assay.

The at least one antibody produced as described above may be utilized simply in the form of the supernatant harvested from the culture medium. Alternatively, the antibodies may be separated and purified.

The antigen located as described above may be detected utilizing any suitable assay technique.

In a further preferred aspect of the present invention the antibody contained in the culture medium may be used for the affinity purification, preferably immuno-affinity purification of antigen.

Accordingly in a preferred aspect there is provided a method for purifying antigen which method includes
  providing
    a crude antigen mixture;
    an antibody against a disease pathogen immobilized on a suitable support, which antibody is produced by a method including
      providing a biological sample from an animal infected with, or challenged by, the pathogen or pathogen extract;
      isolating cells from the biological sample;
      culturing cells in vitro in a suitable culture medium; and
      harvesting antibodies produced from said cells;
    subjecting the crude antigen mixture to an affinity chromatography utilizing the immobilized antibody; and
    isolating the purified antigen so formed.

Antibody can be obtained from the culture supernatant probe by conventional methods. For example methods usually used to purify immunoglobulins from serum or plasma, e.g. precipitation with ammonium sulphate, fractionation with caprylic acid, ion exchange chromatography or by binding and elution from immobilized protein G or protein A may be utilized. Antibody so obtained can then be coupled to suitable supports, e.g. CNBr-activated Sepharose 4B (Pharmacia) Affi-gel (Bio-RAD) or other affinity chromatography supports able to bind proteins.

Immobilized antibody can then be applied to the fractionation and purification of specific antigen from a complex parasite extract by affinity chromatography. After binding of antigen to immobilized antibody, unbound macromolecular species can be washed away from the solid support with, e.g. buffers containing 1.5M NaCl. Subsequently the antigen can be eluted from the affinity column with, e.g. low or high pH buffer or buffers containing chaotropic ions, e.g. 0.5–3.0M sodium thiocyanate.

The application of the antibody probe to affinity chromatography enables sufficient quantities of specific antigens to be rapidly isolated from a complex crude extraction mixture for biochemical characterization, amino-acid sequencing and vaccination of animals for limited protection studies. Application of affinity chromatography for obtaining antigen(s) avoids the difficulties often encountered when applying conventional biochemical techniques to the purification of an antigen about which little or no data is known. It also obviates the need to raise polyclonal or monoclonal antibodies for the purpose of "analytical" affinity chromatography. Large scale preparation may however require the preparation of polyclonal or monoclonal antibodies.

The antigens isolated or located may be used in the preparation of monoclonal antibodies. The monoclonal antibodies may form the basis of a passive treatment of the disease discussed above. Having identified the antigen(s) molecular biology or chemical techniques, e.g. cloning techniques may be used to produce unlimited amounts of this antigen or alternatively synthetic peptides corresponding to different fragments of the identified antigens may be used as a means to produce a vaccine.

Accordingly in a preferred aspect of the present invention there is provided a method for preparing a synthetic antigenic polypeptide against a disease pathogen, which method includes
  providing
    a cDNA library, or genomic library derived from a sample of a disease pathogen; and
    an antibody probe selected from the group consisting of
      an antibody probe as described above;
      a monoclonal antibody derived therefrom, or a derivative thereof;
  generating synthetic polypeptides from the cDNA library or genomic library;
  probing the synthetic polypeptides with the antibody probe;
  probing the cDNA or genomic library with the antibody probe; and
  isolating the synthetic antigenic polypeptide detected thereby.

Either cDNA or genomic libraries may be used. The cDNA or genomic libraries may be assembled into suitable expression vectors that will enable transcription and the subsequent expression of the clone DNA, either in prokaryotic hosts (e.g. bacteria) or eukaryotic hosts (e.g. mammalian cells). The probes may preferably be selected from:
  (i) synthetic oligonucleotide probes based on the amino acid sequence of the antigen identified and purified as described above,
  (ii) antibodies obtained from the culture medium produced as described above;
  (iii) monoclonal or polyclonal antibodies produced against the antigens identified an purified as described above.
  (iv) recombinant or synthetic monoclonal antibodies or polypeptides with specificity for the antigen, e.g. as described by Ward et al 1989, Nature 241, pages 544–546.

Accordingly in a further aspect of the present invention, there is provided a protective antigen against a disease pathogen prepared by a method including
  providing
    a sample of a disease pathogen; and
    an antibody probe including at least one antibody against a disease pathogen produced by a method including
      providing:

a biological sample from an animal infected with, or challenged by, the pathogen or pathogen extract;
isolating cells from the biological sample;
culturing cells in vitro in a suitable culture medium; and
harvesting antibodies produced from said cells.

The protective antigens may function as diagnostic antigens as discussed below.

Accordingly, in a preferred aspect of the present invention there is provided a protective antigen against *Taenia hydatigena* infections, selected from antigens having approximate molecular weights of 25 and 34 kilodaltons, as hereinafter described. As cross protection between various cestodes has been documented, similar antigens may also be detected in other cestode species, e.g. *T. saginata, T. ovis, T. solium, Echinococcus granulosus*.

In a further preferred aspect of the present invention there is provided a protective antigen against *Haemonchus contortus* infections, having an approximate molecular weight of 67 to 75 kilodaltons, as hereinafter described.

In a further preferred aspect of the present invention there is provided a protective antigen against *Fasciola hepatica* infections, having an approximate molecular weight of 120 to 125 kilodaltons, as hereinafter described.

In a still further preferred aspect of the present invention there is provided a protective antigen against *Corynebacterium pseudotuberculosis* infections, having an approximate molecular weight of 38 to 40 kilodaltons, as hereinafter described. This antigen is a protein antigen.

Accordingly, in a further aspect of the present invention there is provided a process for producing a monoclonal antibody against an antigen of a disease pathogen which method includes
providing
a B cell capable of producing antibodies against said antigen and obtained from an animal immunized with a protective antigen against the disease pathogen as described above; and
a myeloma cell;
fusing the B cell with the myeloma cell;
propagating a hybridoma formed thereby, and harvesting the antibody produced by said hybridoma.

In a still further aspect the present invention provides a method for preventing diseases in animals, which method includes administering to an animal an effective amount of at least one protective antigen prepared by a method as described above. Preferably the protective antigen is an antigen against a disease pathogen selected from the group consisting of *Taenia hydatigena., Haemonchus contortus, Fasciola hepatica* or *Corynebacterium pseudotuberculosis* as herein described.

In a still further aspect of the present invention there is provided a method for the treatment of diseases in animals, which method includes administering to an animal a therapeutically effective amount of a monoclonal antibody to a protective antigen produced as described above.

The present invention further provides a vaccine composition including a prophylactically effective amount of at least one protective antigen against a disease pathogen selected from the group consisting of *Taenia hydatigena., Haemonchus contortus, Fasciola hepatica* or *Corynebacterium pseudotuberculosis* as hereinafter described.

The present invention further provides a vaccine or veterinary composition including a therapeutically effective amount of at least one monoclonal antibody prepared as described above.

The vaccine or veterinary compositions according to the present invention may be administered orally or may be administered parenterally (for example by intramuscular, subcutaneous or intravenous injection). The amount required will vary with the antigenicity of the active ingredient and need only be an amount sufficient to induce an immune response typical of existing vaccines.

Reactive experimentation will easily establish the required amount. Typical initial doses of vaccine or veterinary compositions may be approximately 0.001–1 mg active ingredient/kg body weight. The dose rate may increase or multiple doses may be used as needed to provide the desired level of protection.

The vaccine or veterinary composition according to the present invention may further include a veterinary acceptable carrier, diluent or excipient therefor. Preferably the active ingredient may be suspended or dissolved in a carrier. The carrier may be any solid or solvent that is non-toxic to the animal and compatible with the active ingredient. Suitable carriers include liquid carriers, such as normal saline and other non-toxic salts at or near physiological concentrations, and solid carriers, such as talc or sucrose. Adjuvants, such as Freund's adjuvant, complete or incomplete, or immunomodulators such as cytokines may be added to enhance the antigenicity of the antigen if desired. When used for administering via the bronchial tubes, the vaccine is suitably present in the form of an aerosol.

In a still further aspect of the present invention there is provided a diagnostic kit including a diagnostic antigen against a disease pathogen identified and purified as described above.

The diagnostic kit may be utilized to detect infections in animals including *Taenia hydatigena, Haemonchus contortus, Fasciola hepatica* and *Corynebacterium pseudotuberculosis*.

The present invention will now be more fully described with reference to the following examples. It should be understood, however, that the description following is illustrative only and should not be taken in any way as a restriction on the generality of the invention described above.

BRIEF DESCRIPTION OF THE FIGURES

FIG. 1A—*H. contortus*

Western blot from a 12.5% SDS polyacrylamide gel showing antigens in the $L_3$ and $L_4$ preparation (arrowed) identified by culture supernatant from immune-challenged sheep. Prestained molecular weight standards (BIORAD) are indicated.

FIG. 1B—*H. contortus*

Western blot from a 7.5 to 15% gradient SDS-polyacrylamide gel showing antigens in the $L_4$ preparation (arrowed) identified by culture supernatant from immune-challenged sheep. Prestained molecular weights (Bio-Rad) are indicated.

Figure 2:
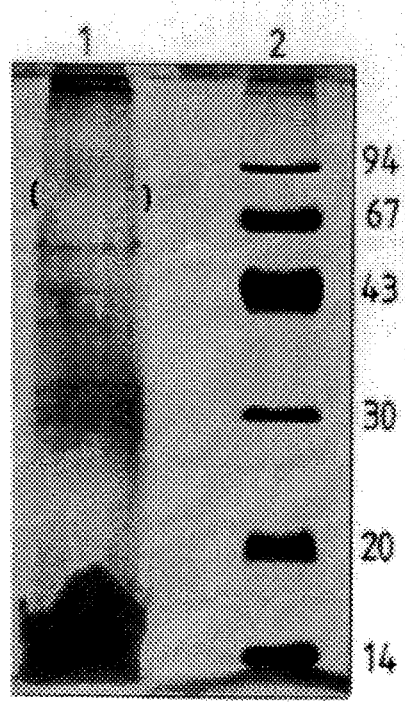

FIG. 2—*H. contortus*

Silver-stained gel of affinity purified proteins on a 12.5% SDS-polyacrylamide gel under non-reducing conditions. The affinity-purified proteins are in lane 1 and molecular weight standards (Pharmacia) are given (mw×10$^{-3}$). The region of antibody reactivity is bracketed.

Figure 3:
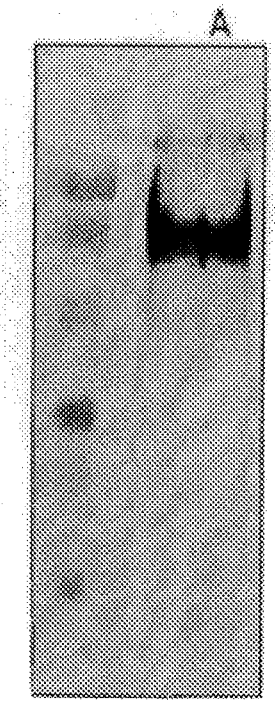

FIG. 3—*H. contortus*

Western blot of affinity isolated antigens after probing with culture supernatant from a immune-challenged animal (Lane A). Prestained molecular weight markers (Bio-Rad) as in FIG. 1.

Figure 4:
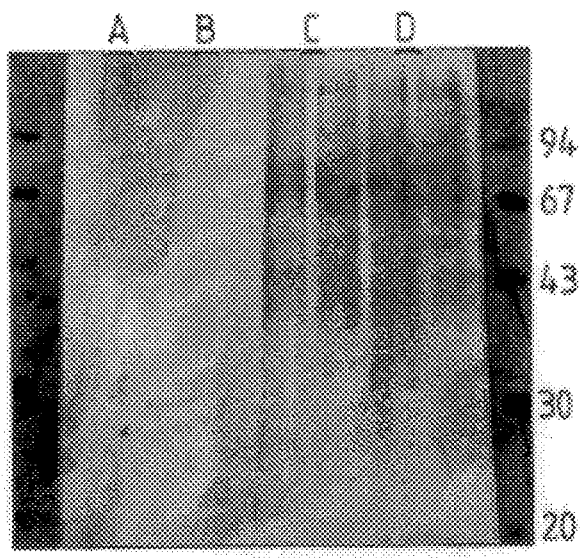

FIG. 4—*H. contortus*

Western blot of affinity isolated antigen after incubating with Proteinase K (lanes A), trypsin (lanes B), Glycopeptidase F (lanes C) and control (no enzyme) (Lanes D). Molecular weights (Pharmacia) (mw×10⁻³) are indicated.

Figure 5:
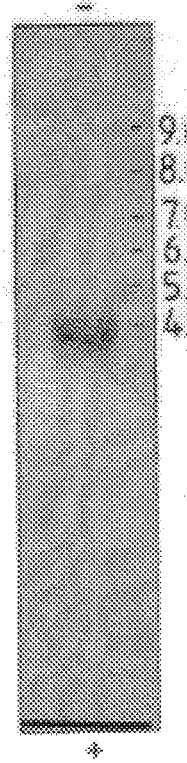

FIG. 5—*H. contortus*

IEF capillary transfer to nitrocellulose from an agarose IEF gel ampholyte range 3–5 and probed with culture supernatant from an immune animal. Ph range using IEF standards (Bio-Rad) are given.

Figure 6:

FIG. 6—*F. hepatica*

Western blot from a 7.5–15% SDS-PAGE gel.

Figure 1A:
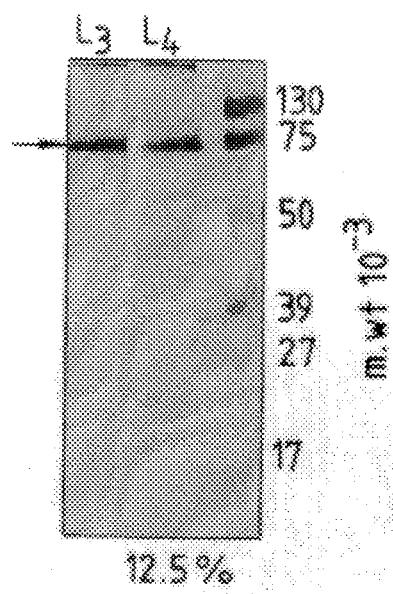
Figure 1B:
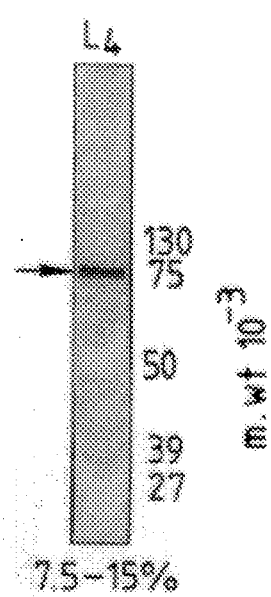

MW=prestained molecular weight markers (BIORAD) as in FIG. 1.

Lanes 1 & 4—NEJ antigen preparation.

Lanes 2 & 5—Adult fluke antigen preparation.

Lanes 3 & 6—12 day old fluke antigen preparation.

Lanes 1, 2 & 3 were probed with culture supernatant from HLN cells of infected cattle.

Lanes 4, 5 & 6 were probed with a mixture of culture supernatants from HLN of 10 day challenged sheep with an abbreviated or chronic primary infection.

Brackets=antigen claimed.

FIG. 7—*F. hepatica*

Figure 7A:
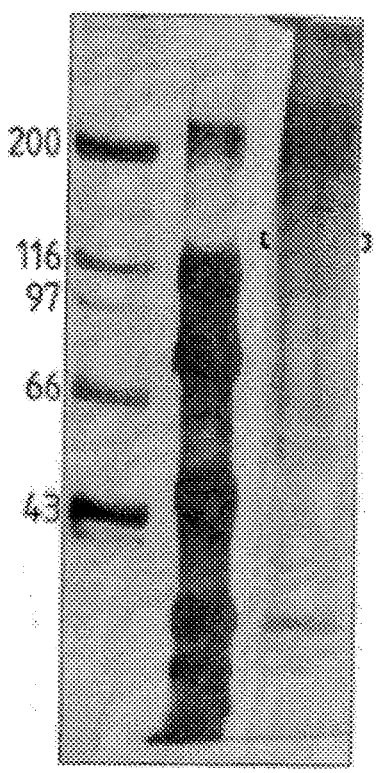

FIG. 7(A) 7.5–15% SDS-PAGE gel stained with silver nitrate.

lane 1—high molecular weight markers (BIORAD) in reducing sample buffer.

lane 2—prestained molecular weight markers (BIORAD).

lane 3—Newly encysted juvenile (NEJ) antigen preparation in non-reducing sample buffer.

Brackets=position of antigen claimed.

Figure 7B:

FIG. 7(B) 10% SDS-PAGE gel stained with silver nitrate.

lane 1—normal mouse serum in non-reducing buffer.

lane 2 & 3: n-butanol extracted antigen preparation in non-reducing sample buffer. Pellet (2) and supernatant (3) after 100,000 g spin for 50 minutes.

lane 4 & 5: Supernatant from NEJ sonicate. Pellet (4) and supernatant (5) after 100,000 g spin for 50 minutes.

Brackets=antigen claimed.

Figure 8:
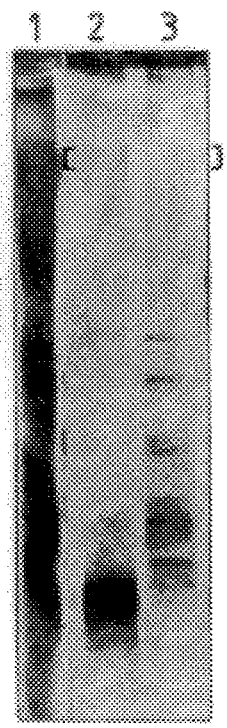

FIG. 8—*F. hepatica*

10% SDS gel stained with silver nitrate.

Bound (lane 2) and non-bound (lane 3) fraction after affinity purification of sonicated NEJ antigen preparation.

Brackets=position of antigen claimed.

Lane 1=prestained molecular weight markers (BIORAD) as in FIG. 1.

FIG. 9—*T. hydatigena*

Western blot from a 10% SDS-PAGE gel of oncosphere antigen in non-reducing sample buffer probed with culture supernatant from liver lymphocytes isolated from immune-challenged (+) or non-challenged (−) sheep.

FIG. 10—*T. hydatigena*

Probing of Western blots of oncosphere antigen (0) at dilutions of ½ and ¼ and probing of Western blots of bladderwall metacestode antigen (B) preparations and scolex metacestode antigen (S) preparations with the positive culture supernatant as in FIG. 9. 10% SDS-PAGE gel.

Arrows=antigens claimed

Sigma molecular weight markers run in reducing buffer.

Figures 11, 12:
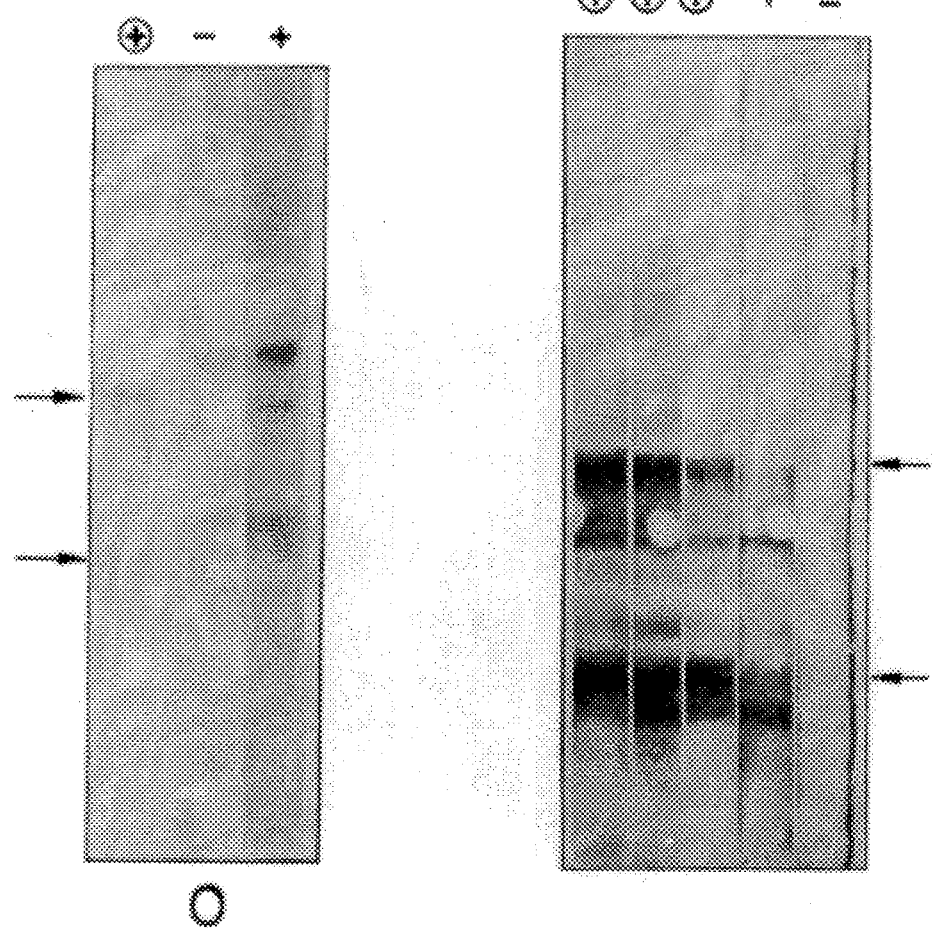

FIG. 11—*T. hydatigena*

Probing of Western blots of oncosphere antigen with negative serum (−) or positive serum (+) taken from the same sheep at the same time after infection as the positive culture supernatant (+). 12% SDS-PAGE gel. Serum dilution: 1/20.

FIG. 12—*T. hydatigena*

Western blot of oncosphere antigens probed with negative (1) or positive (2) serum or culture supernatant from leucocytes isolated from liver (3), hepatic lymph node (4) or prescapular lymph node (5) of recently infected animals. 10% SDS-PAGE gel.

FIG. 13—*C. pseudotuberculosis*

Western blot on nitrocellulose from 12.5% SDS-PAGE-Samples solubilized in reducing buffer.

Strip A. Stained with amido black.
 Lane 1. Molecular weight standards.
 Lane 2. WA 1030 isolate cell extract.
Strip B. WA 1030 isolate cell extract.
 Lane 1. Serum taken immediately prior to infection.
 Lane 2. 2 days past infection
 Lane 3. 4 days past infection
 Lane 4. 7 days past infection
 Lane 5. 11 days past infection
 Lane 6. 14 days past infection
Arrows=protein antigen claimed.

FIG. 14—*C. pseudotuberculosis*

Isoelectric focusing of *C. pseudotuberculosis* antigen. Antigen has pI between 6.8–6.9.

FIG. 15—*H. contortus*

Purification of the 70–90 kD surface glycoprotein from *H. contortus* antigen by size exclusion chromatography on an Ultraspherogel SEC2000 column connected to Hewlett Packard 1090 liquid chromatograph. The flow rate was 0.5 ml per minute and the column effluent was monitored at 232 nm and 280 nm. The elution buffer was 100 mM NaCl, 10 mM Tris Hcl pH 7.4.

Figure 15A:
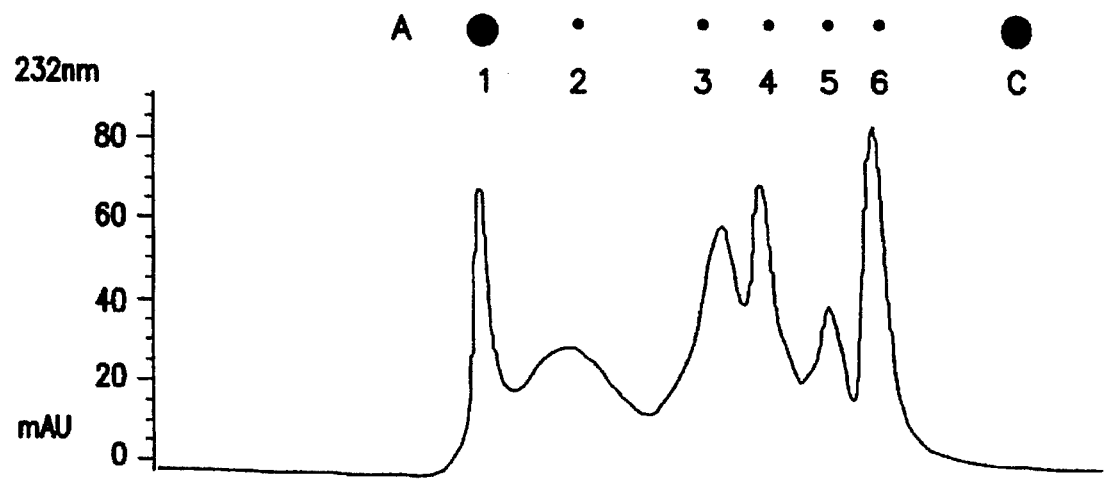

FIG. 15a shows a dotblot of the fractions using ASC probes. The antigenic material is clearly present in faction 1 which corresponds to the first peak. C is a control dot of the extract before purification.

Figure 15B:
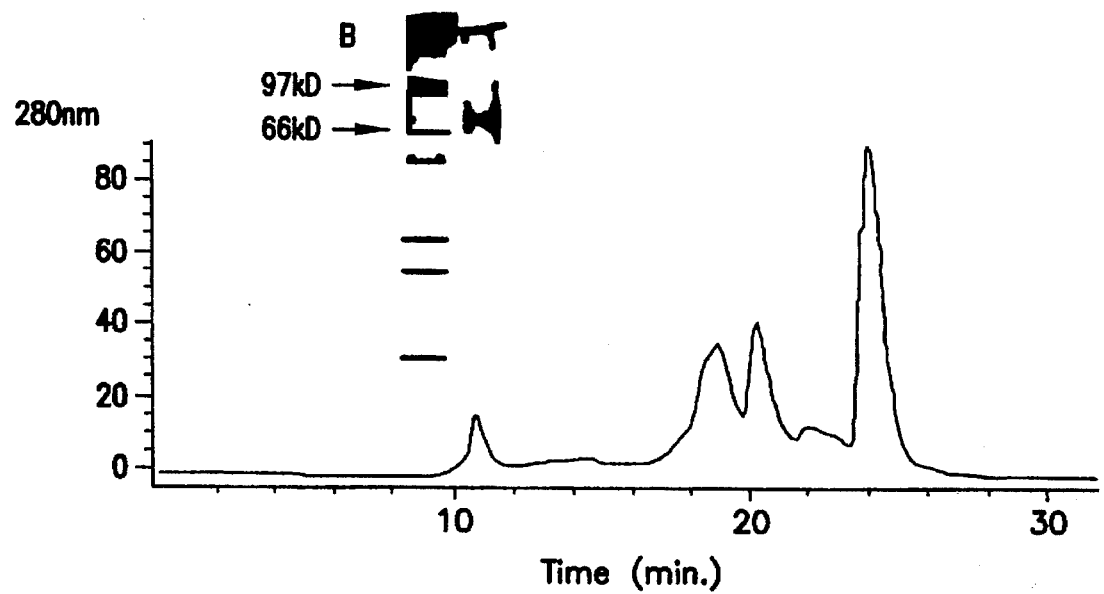

FIG. 15b: SDS PAGE and Coomassie blue staining of the same fractions showing that the molecular weight of the protein in the antibody positive peak is 70–90 kD and the band has a characteristic H-shape.

Figure 16:
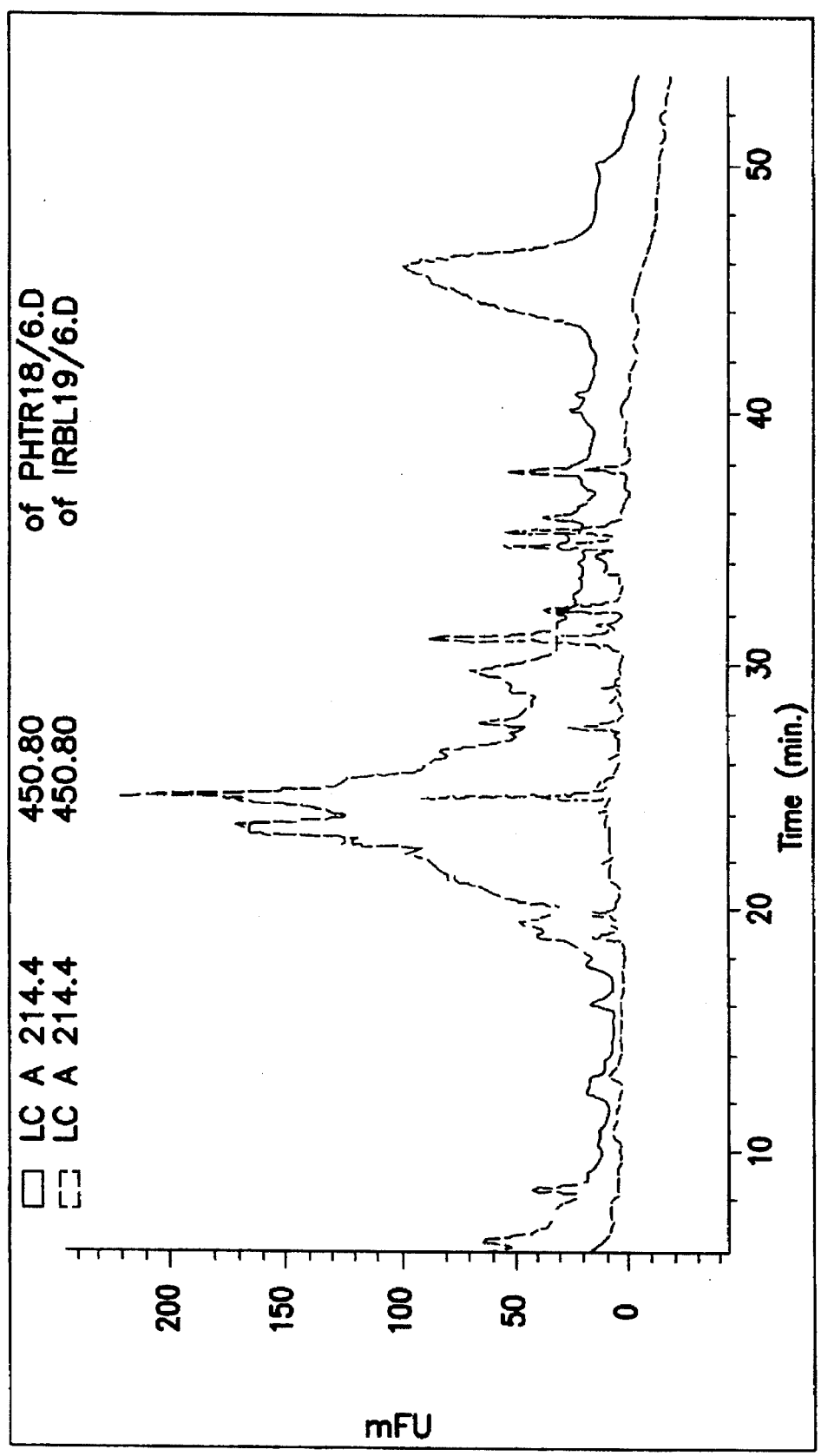

FIG. 16—*H. contortus*

HPLC chromatogram of *Haemonchus contortus* antigen tryptic peptides.

Figure 17:
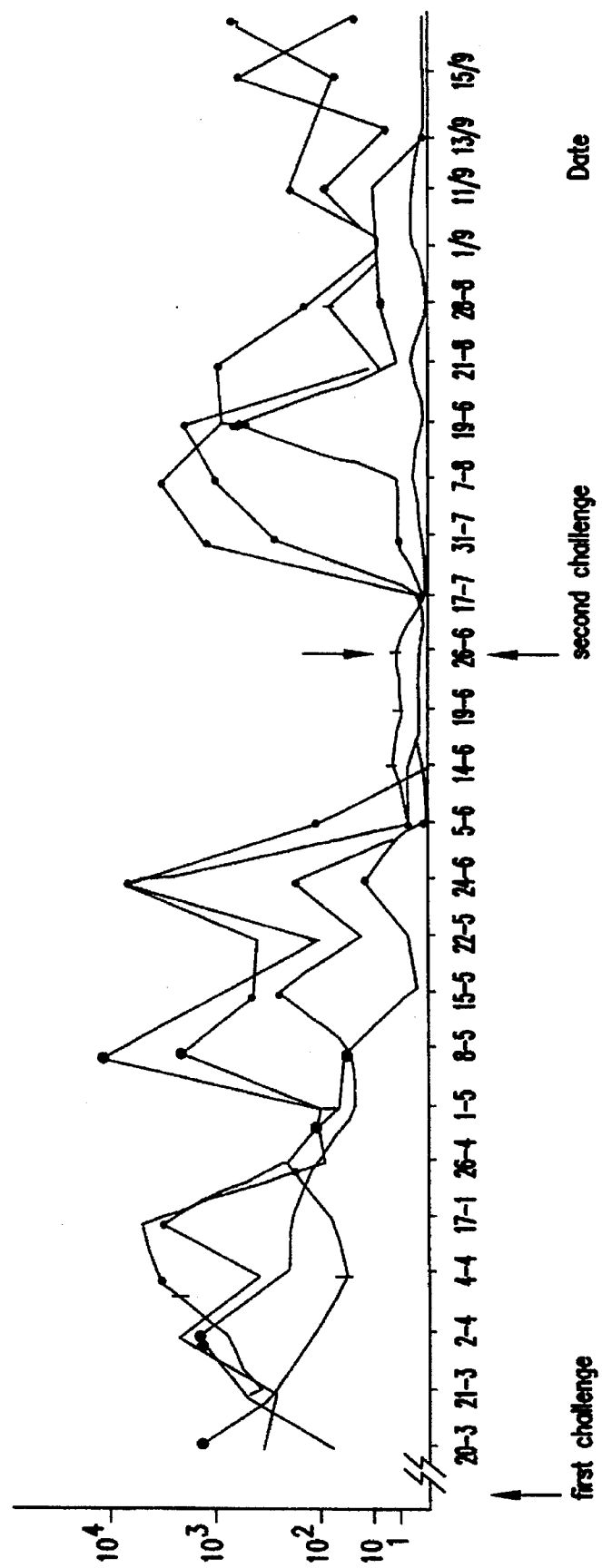

FIG. 17—*H. contortus*

Vaccination trial 1: Mean eggs per gram from vaccinates and controls.

−=vaccinates (v) −=controls (c).

Figure 18B:
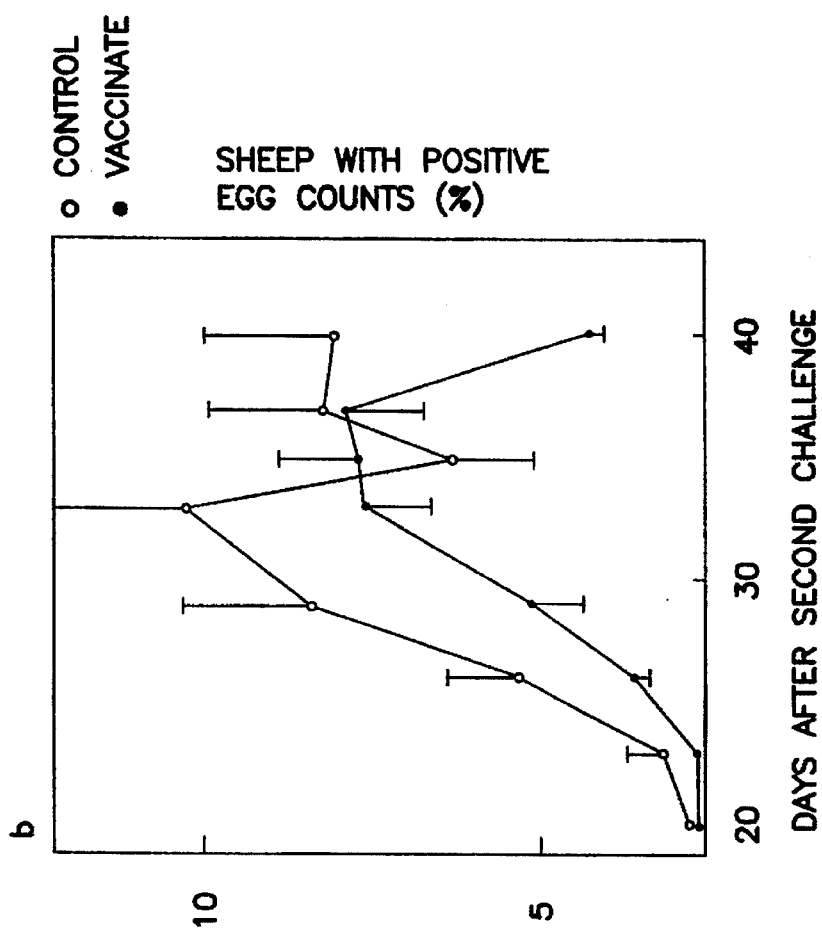
Figure 18A:
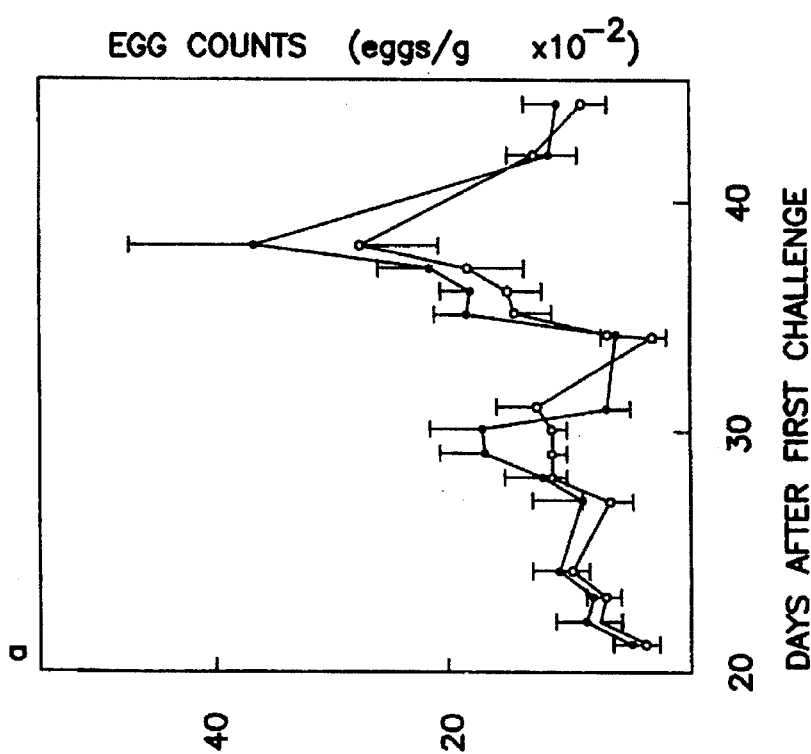

FIG. 18—*H. contortus*

Vaccination trial 2: (a) Mean (SEM) eggs per gram from vaccinates and controls after the first challenge, (b) Mean (SEM) eggs per gram from vaccinates and controls after the second challenge.

Figure 19:
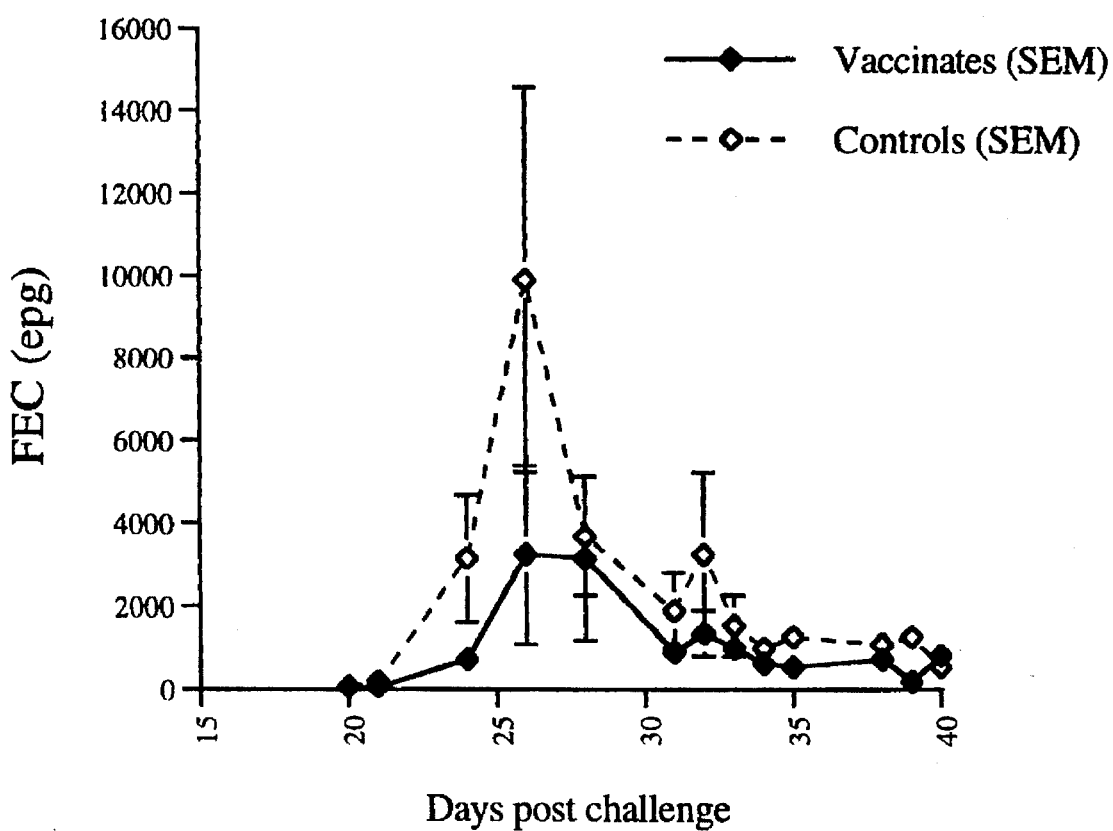

FIG. 19—*H. contortus*

Vaccination trial 3: Mean eggs per gram faeces for vaccinates and controls from Trial 3.

FIG. 20a—*H. contortus*

Vaccination trial 4: Mean (SEM) eggs per gram faeces for vaccinates and controls.

FIG. 20b—*H. contortus*

Vaccination trial 5: Mean (SEM) faecal egg counts of vaccinates and controls.

Figure 21:
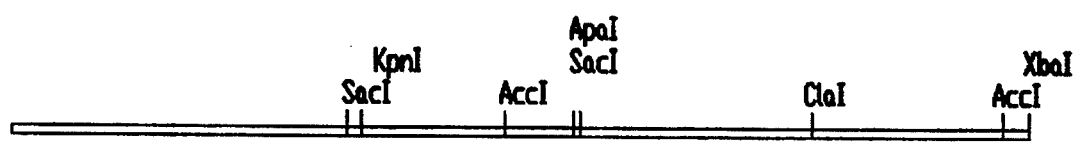

FIG. 21—*C. pseudotuberculosis*

Restriction map of the open reading frame of the 40 KD gene from *C. pseudotuberculosis*.

FIGS. 22A and 22B—*C. pseudotuberculosis*

Complete nucleotide sequence and predicted amino acid sequence of the 40 KD protein from *C. pseudotuberculosis*. Underlined section indicates leader sequence.

FIG. 23—Bacteria

Southern blot of 40 KD ORF probing genomic DNA from different bacterial species digested with EcoR1

LANE 1 *C. pseudotuberculosis*

2 *C. diptheriae*

3 *C. diptheriae Intermedius*

4 *C. diptheriae Gravis*

5 *Listeria monocytogenes*.

Figure 24:
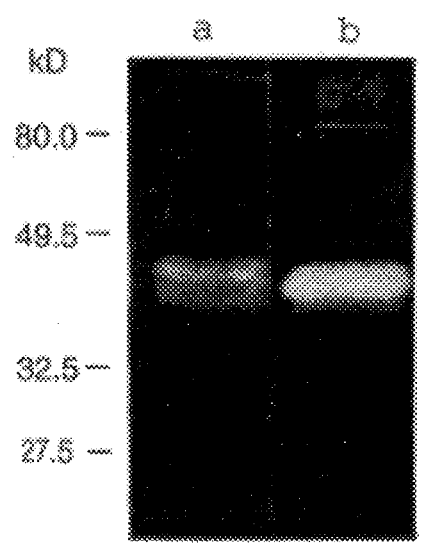

FIG. 24—*C. pseudotuberculosis*

Protease activity of 40 kDa *C. pseudotuberculosis* antigen on gelatin substrate gels. —Track (a)—Native 40 kD protein. Track (b)—Recombinant 40 kD protein.

Figure 25:
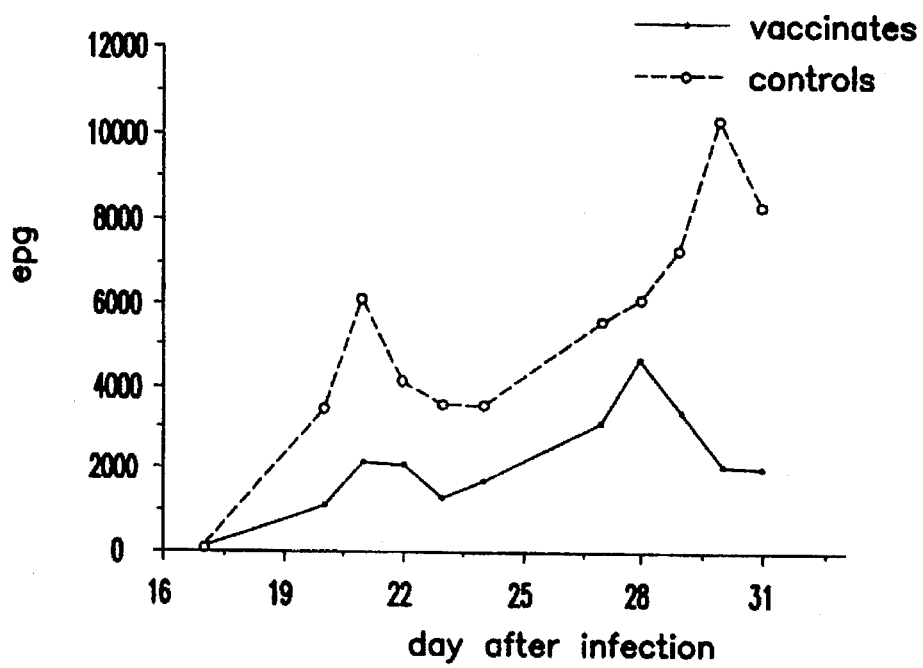

FIG. 25—*O. circumcincta*

Vaccination trial 1: Mean eggs per gram faeces for vaccinates and controls.

Figure 26:
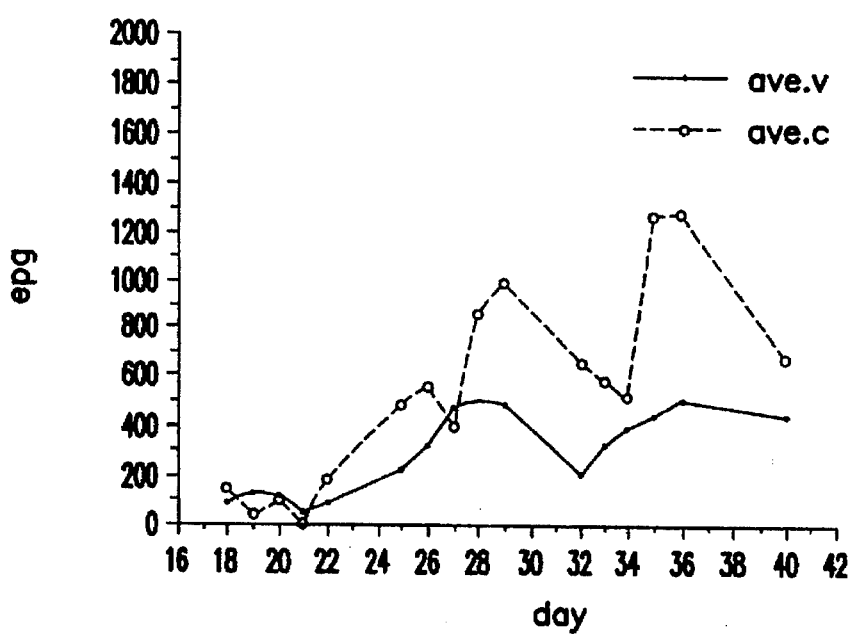

FIG. 26—*O. circumcincta*

Vaccination trial 2: Mean eggs per gram faeces for vaccinates or controls.

EXAMPLE 1

Haemonchus contortus

*Haemonchus contortus* is an intestinal parasite of sheep that localizes in the abomasum (fourth stomach). Late larval and adult stages of the parasite feed on whole blood. The parasite is responsible for sizeable economic loss to the sheep industry in Australia and considerable loss overseas and is a potentially fatal disease. Despite these losses no successful vaccine has been developed in the prior art against this parasite.

Parasite and Experimental Animals

*H. contortus* third stage larvae ($L_3$) were collected from faecal cultures of donor sheep experimentally infected with the parasite. Immune animals were obtained by repeatedly infecting sheep with *H. contortus* larvae and then monitoring faecal egg output. When a challenge dose produced no eggs in the faeces the animal was said to be immune. Once immune, the sheep were left for a period of at least four weeks before being challenged with 50,000–200,000 $L_3$ larvae and then killed five days post challenge.

Preparation of Culture Supernatants

Abomasal lymph nodes, draining the area of infection (abomasum) were removed and cell suspensions prepared as described for *T. hydatigena* below. Bulk cultures of 10–50 ml were set-up in culture flasks (Miles) at concentration of 2–4×$10^6$ cells/ml in culture medium. Preliminary experiments established that most of the antibodies in the culture supernatant were produced by the antibody secreting cells present in the in vivo stimulated lymph nodes and that this was not further increased by stimulation with pokeweed mitogen (PWM). PWM was therefore deleted form the cultures and culture supernatants were harvested after a five day incubation of cells at 37° C. in a 5% $CO_2$ atmosphere and stored at –20° C. until used.

Stage-Specific Recognition of Antigens by Culture Supernatant

Third stage larvae *H. contortus* were exsheathed in 0.05% sodium hypochlorite for 10 minutes at 37° C. to remove the second stage sheath. The larvae were then repeatedly washed and centrifuged at 3,000 g for 10 minutes in phosphate buffered saline (PBS) pH 7.4. After the sixth wash they were transferred to 500 ml of DME medium pH 6.8 in the presence of 200 U/ml penicillin and 0.2 ug/ml streptomycin and cultured at 39° C. with 20% $CO_2$ in air for 5 days. The culture media was then centrifuged at 3,000 g for 15 minutes at 20° C. $L_3$, in vitro switched $L_4$ and adult parasites were removed and mechanically homogenized using a teflon pestle and a ground-glass tube for 20 minutes at 4° C. in the presence of 0.1% Empigen zwitterionic detergent (Calbiochem) in PBS and 5 mM phenylmethyl sulfonyl fluoride (PMSF). The homogenized larvae were immediately aliquoted and stored at –70° C. Frozen aliquots were thawed and mixed 1:1 with SDS non-reducing sample buffer and boiled for 5 minutes before being centrifuged for 2 minutes at 5,000 g and run on a 12.5% SDS-polyacrylamide mini gel (Bio-Rad) according to the method of Laemmli (1970). The gel was then electrophoretically transferred to nitrocellulose (Kerlero de Rosbo et al, 1984) and probed with serum or culture supernatants from abomasal lymph node cells from immune challenged or non-challenged immune sheep. Western blots were blocked with 0.5% Tween 20 in PBS and all washes were done in 0.05% Tween 20 in PBS. The second antibody was a rabbit anti-sheep immunoglobulin coupled to horse-radish peroxidase (Dako) and then developed with 3'3-diaminobenzidene (Sigma) and hydrogen peroxide.

Larval antigens were detected between approximately 67–75 kilodaltons (Kd) in the in vitro cultured fourth stage larvae ($L_4$), and third stage ($L_3$) exsheathed larvae of *H. contortus* when probed with culture supernatant from immune-challenged sheep (FIG. 1). No antigens were identified at the molecular weights mentioned above for adult Haemonchus preparations (data now shown). There was no reaction when supernatant from non-challenged immune sheep was used to probe the blots (not shown), indicating that all the antibodies produced in the culture supernatant of the immune-challenged sheep were induced by the 5 day in vivo challenge. Similar probing of the Western blots with serum of the same animals taken at the same time reacted with several bands in all 3 parasite stages but did not highlight the 67–75 kD antigen (not shown). Also, as opposed to culture supernatant, no difference could be detected between serum of immune-challenged or immune non-challenged sheep.

Preparation of $L_4$ Antigen for Affinity Purification

Crude antigen for affinity purification was prepared by shearing in vitro switched $L_4$ larvae with a polytron tissue homogenizer for 30 seconds on ice in the presence of 0.05% Empigen in 0.1M Tris pH 8.0 and 5 mM PMSF. After polytron treatment, SDS was added to a final concentration of 2% and the sample boiled for 3 minutes in a water bath, then centrifuged at 35,000 rpm for 30 minutes at 4° C. After centrifugation the SDS was removed from supernatant by precipitating the protein according to "Method A" described by Henderson, Oroszlan and Konigsberg (1979). After SDS removal, 7M Guanidine hydrochloride (IBI) was added to the protein precipitate and allowed to stand for 5 hours on ice. An equal volume of 25% glycerol in distilled water was added and the entire sample dialysed against PBS and 0.05% Empigen pH 7.4. The sample was then applied to an affinity column.

Affinity Purification of Antigen

An affinity column was constructed to isolate the specific antigen by first removing antibodies from the culture supernatant of immune-challenged sheep using both Protein G Sepharose (Pharmacia/LKB) and donkey anti-sheep antibodies (Dako) coupled to Affi-prep (Bio-Rad) according to manufacturer's specifications. The purified antibodies were then coupled to Affi-prep (Bio-Rad) according to the manufacturer's instructions and the column equilibrated in PBS and 0.05% Empigen detergent.

$L_4$ antigens were loaded onto the affinity column and unbound proteins removed using 0.5M NaCl pH 7.4 and 0.05% empigen. Bound proteins were eluted using 1M NH$_4$SCN (Ajax) in PBS. The eluate was monitored by OD$_{280}$. After elution the sample was extensively dialysed against 0.005M Tris pH 8.3, lyophilized and stored at −70° C. Samples were resuspended in distilled water and used for further analysis.

Silver-Staining and Coomassie Staining of Affinity Isolated Antigen

On convention SDS-Page gels several bands could be seen when silver staining the gels according to the method of Morrissey (1981) FIG. 2. Immunoblotting and probing with culture supernatants from immune-challenged sheep resulted in a very intense antibody response in the 67–75 kd region in the affinity isolated preparation (FIG. 3). However no bands on either silver or coomassie stained gels could be positively correlated with this region of antibody reactivity. It would therefore appear that this particular molecule does not stain with the conventionally used protein stains.

Enzyme Ddigests

6 μg of affinity isolated antigen from fourth stage larvae was incubated overnight at 37° C. with either Glycopeptidase F (20 μl) (Boehringer Mannheim) and proteinase K (10 μg) (Sigma) in 0.1M Na-phosphate buffer pH 8.0 containing 10 mM EDTA, 0.1% SDS, 0.5% Triton-X-100 and 0.1% β-mercaptoethanol. In addition, the antigen was incubated with trypsin (10 μg) (Difco) in PBS. After incubation, all samples were mixed with SDS non-reducing buffer, boiled for 5 minutes and loaded onto a 12.5% SDS-polyacrylamide gel, transferred to nitrocellulose and probed with culture supernatant as previously described. Both proteinase K and trypsin treatment resulted in breakdown of the protein such that there was no recognition by antibodies in the culture supernatant (lanes A and B respectively). N-glycanase had no effect on the antigen producing the same result as the control incubation (lanes C and D). This indicates that the antigen had a protein component which is degradable by proteinase K and trypsin, however the protein does not appear to contain asparagine-linked glycans under these conditions.

Iso-Electric Point of the Antigen

Thin-layer iso-electric focusing (IEF) gels were prepared using a plastic template (Corning Immunoelectrophoresis plate) according to the method of McLachlan and Cornell (1978). Each IEF gel consisted of 0.95% w/v of IEF agarose (Bio-Rad), 11.4% w/v D-sorbitol (Sigma), 4.8% carrier ampholytes (Bio-Rad) range 3–5 or 3–10 and distilled water. The water, sorbitol and agarose were boiled, then placed on a 56° C. water bath. The ampholines were then added, the solution poured onto the template and a piece of Gelbond (FMC Pharmacia) overlayed. The template was placed in a plastic bag and stored at 4° C. for at least 2 hours before use.

One μl of affinity purified antigen was applied and the gel was run at one watt constant power for 45 minutes. Upon completion of the run the gel was overlayed with nitrocellulose (Schleicher and Schuell) followed by several pieces of filter paper and a glass plate to act as a weight. Proteins the diffused from the gel to the membrane for one hour after which the membrane was blocked and probed with culture supernatant as previously described. The results indicated the presence of a highly acidic protein with an iso-electric point below 4.65 as indicated by IEF standards (Bio-Rad) FIG. 5.

EXAMPLE 2

Fasciola hepatica

Fasciola hepatica (liver fluke) is a parasite from the trematode family which can develop in the liver and bile ducts of many mammals and is of particular economic importance to the sheep and cattle industry. No prophylactic treatments such as vaccines against liver fluke are on the market. While sheep do not develop an immunity against F. hepatica, cattle can become partially resistant against reinfection. Although the mechanism of resistance in cattle has not been fully elucidated one possibility is that cattle recognize a different (protective) antigen than sheep. The technique described above was therefore used to study the differential antigen recognition between sheep and cattle.

Antigen Preparations

1. Newly Encysted Juveniles (NEJ)

F. hepatica metacercariae (Mc) were purchased from Baldwin Aquatics (Monmouth, Oreg., U.S.A.). Metacercariae were excysted by suspension in 20 ml DME medium containing 100 mg Na-Tauro-cholic acid, 80 mg L-cysteine. The suspension was gassed in a mixture of 40% $CO_2$, 10% $O_2$ and 50% $N_2$, incubated at 37° C. and NEJ collected after filtration through metal mesh. Sedimented NEJ were resuspended in phosphate buffered saline containing protease inhibitors (PBS-PI) (5 mM Iodoacetamide and 1 mM PMSF) and sonicated. Aliquots were stored at −70° C.

2. Juvenile Flukes

Mice were infected orally with 30 Mc and killed 12 days later. Macerated livers were washed through a tea strainer and the juvenile flukes were recovered by differential centrifugation. Antigen was prepared as above.

3. Adult Flukes

Infected livers from sheep or cattle were obtained from an abattoir. Adult flukes were recovered from the bile ducts, homogenized with tissue grinder, aliquoted and frozen at −70° C.

SDS-Polyacrylamide Gel Electrophoresis (SDS-PAGE) and Western Blotting

As for Haemonchus but only 7.5–15% gradient gels or 10% SDS-Page gels were run. All antigens were mixed 1:1 with non-reducing buffer. Bovine and ovine antibodies were detected using peroxidase-conjugated rabbit anti-bovine or sheep immunoglobulins (DAKO) respectively.

Butanol Extraction

Newly excysted juveniles suspended in PBS-PI were sonicated and spun for 10 minutes at 5000 g. The supernatant was used for affinity purification as described later. The pellet was resuspended in PBS-PI and an equal volume of cold n-butanol was added. The mixture was incubated on ice for 10 minutes with occasional vortexing and then spun at 5000 g for 5 minutes. The water-soluble fraction was collected in the bottom layer.

Affinity Purification

Antibodies were purified from the culture supernatant of infected cattle (see later) using Sepharose bound protein G (Pharmacia) and used for the preparation of an affinity column essentially as described for H. contortus.

Triton X-100 R-S (Sigma) was added to a NEJ sonicate supernatant (see above) at a final concentration of 2%. The sonicate was loaded onto the affinity column and unbound fractions washed through with PBS containing 0.1% Triton X-100 R-S and 1 mM PMSF followed by 1.5M NaCl. The bound fraction was eluted with 2M NH$_4$SCN in PBS, dialysed against distilled water and freeze dried. Freeze-dried fractions were resuspended in PBS for further use.

Preparation of Culture Supernatant

Three sheep and three cattle were infected orally with 400 metacercariae. 18 days later they were dosed with FASINEX 120 (CIBA-GEIGY Australia Ltd.) to eliminate the primary infection. The animals were left for an additional 35 days before being challenged orally with 400 metacercaria. They were killed 10 days after challenge. Hepatic lymph nodes (HLN) were removed, cells isolated and incubated at 2–4× $10^6$ cells/ml in culture medium with PWM as described for *T. hydatigena* and the supernatants harvested after 7 day in vitro culture. Additional culture supernatant was collected from HLN cells of sheep carrying an untreated primary *F. hepatica* infection (80 Mc) and challenged with 300 Mc 10 days before slaughter.

Results

Probing of Western blots with culture supernatant from HLN cells of infected cattle resulted in strong antibody reactivity to a doublet antigen in a NEJ antigen preparation located slightly above the highest prestained molecular weight marker (FIG. 6). Only one band at the higher molecular weight level of the NEJ doublet was consistently present in 12 day old fluke preparations while a similar band in the adult fluke preparation could not be reliably detected in several repeat experiments. In contrast, when the same antigen preparations were probed with culture supernatant of HLN cells of similarly infected sheep or a mixture of this culture supernatant with culture supernatant from chronically infected and challenged sheep no such reaction was observed although other bands were strongly recognized (FIG. 6).

Unlike the restricted reactivity of the culture supernatant, similar Western blots probed with serum taken from the same animals at the same time reacted much more diffusely with a number of bands in all 3 parasite stages and no obvious difference between cattle and sheep serum could be observed (not shown).

Silver staining of the total NEJ preparation did not clearly stain the antigen recognized by the cattle culture supernatant suggesting it is a minor component of the total molecular make-up of the parasite (FIG. 7a). By measuring the position of the antigen on a replicate Western blot relative to the highest prestained molecular weight marker, its approximate molecular weight on SDS-PAGE gel using BIORAD high MW markers as standards was calculated at 120–125 Kd. Clear silver staining of the doublet in the NEJ preparation could be seen when a n-butanol extracted soluble fraction of a NEJ sonicate pellet was run on an SDS-PAGE gel (FIG. 7b).

Affinity purification on the bovine antibody column resulted in a clear depletion of the antigen from the non-bound fraction and high enrichment in the bound fraction (FIG. 8). In addition there was also a strong low molecular weight (±24 Kd) band in the bound fraction which also reacted strongly with the cattle culture supernatant on a Western blot (not shown) suggesting that the low MW band was due to breakdown of the 120–125 Kd antigen during the affinity procedure.

EXAMPLE 3

*Taenia Hydatigena*

Materials and Methods

Parasite and Experimental Animals

*T. hydatigena* eggs were collected from mature worm segments after purging of infected dogs with arecoline hydrobromide. 2 year old sheep kept on farms were used. At this age sheep have generally acquired immunity to *T. hydatigena* through natural exposure and this was confirmed in preliminary experiments. Positive sera and positive culture supernatants were collected from sheep killed 13 days after intraruminal injection of 40–50,000 *T. hydatigena* eggs. Negative culture supernatants were collected from sheep without prior challenge infection. Negative serum was collected from 5 month old sheep reared under wormfree conditions.

Preparation of Leukocyte Suspensions

Liver leukocytes were recovered by the following procedure. The sheep liver was removed and perfused via the portal vein with 1 liter of phosphate buffered saline (PBS) at room temperature followed by 0.5 liter of cold PBS with continuous and gentle massaging of the liver. This procedure resulted in complete blanching of the entire liver. Approximately 100 g of liver tissue was homogenized in a foodprocessor (Goldair, Australia) at low speed for 8–10 sec. The homogenized liver was then pushed through metal mesh, left to sediment for 8–10 min and filtered through cotton gauze. The cells were washed twice by centrifugation at 400 g for 8 min, followed by a low spin at 10 g for 5 min. to remove small clumps and the majority of hepatocytes. The supernatant of the last spin was collected and the remaining hepatocytes and dead cells removed by centrifugation over Ficoll/Isopaque gradients.

Leukocytes were also recovered from lymph nodes by cutting and teasing the nodes over a fine wire mesh. Dead cells and clumps were removed by centrifugation over Ficoll.

Preparation of Culture Supernatant

Leukocytes were resuspended at a concentration of 2–4× $10^6$/ml in culture medium consisting of DME to which was added 10 mM HEPES, 100 u/ml penicillin, 100 µg/ml streptomycin, $2.5 \times 10^{-5}$M 2-mercaptoethanol, 2 mM glutamine, 1 mM pyruvate and 10% fetal calf serum. Two ml cultures were set up in 24 well Linbro plates, stimulated with 25 ug/ml of pokeweed mitogen (PWM, Gibco Labs., Grand Island, N.Y.) and incubated at 37° C. in a 5% $CO_2$ atmosphere. After 7 days the cultures were pooled and the cells sedimented by centrifugation. The supernatant was stored at −20° C. until used.

Preparation of Antigens (a) Oncosphere Antigen (O)

*T. hydatigena* eggs recovered from mature worm segments were hatched with sodium hypochlorite and the released oncospheres were purified over 100% Percoll. A total of $2.3 \times 10^5$ oncospheres were resuspended in 1 ml PBS containing protease inhibitors (PBS-PI) (5 mM iodoacetimide and 1 mM phenyl methyl sulphonyl-fluoride) and frozen at −20° C. This preparation was later thawed, sonicated with a MSE 150 W ultrasonic disintegrator (Crawley, England), aliquoted and stored at −20° C.

(b) Metacestode antigens

Metacestodes were collected from the peritoneal cavity of sheep at slaughter. The cyst fluid was removed, scolex and bladderwalls separated and frozen in PBS-PI at −20° C. The preparations were later thawed, homogenized in a Kinematica Homogenizer (Polytron, Luzern, Switzerland), sonicated and centrifuged at 1400 rpm×15 min. The supernatants were aliquoted and frozen at −20° C.

Detection of Antigens by the Western Blotting Technique

40 µl antigen fractions were mixed with 40 µl SDS non-reducing sample buffer, boiled for 5 min. centrifuged for 10 min. at 5000 g and run on a 10 or 12% SDS-polyacrylamide gel. The separated proteins were transferred to nitrocellulose sheets overnight. The sheets were blocked with 3% chicken ovalbumin (OVA) and cut into strips. Specific antigens on the strips were revealed after the following incubation steps:

(1) culture supernatant or serum,
(2) biotinylated donkey anti-sheep Ig (Amersham)
(3) streptavidin-biotinylated horseradish peroxidase complex (Amersham)
(4) peroxidase substrate (0.6 mg/ml diaminobenzidine in PBS containing 0.05% $H_2O_2$).

Reagents were used at manufacturers recommended dilutions.

(1) Probing of Western blots of oncosphere antigen preparations revealed that there were 2 distinct antigen bands specifically recognized by culture supernatant collected from liver leukocytes of recently infected sheep (+) that were not recognized by culture supernatant collected from liver leucocytes of unchallenged sheep (−) (FIG. 9, arrows). These 2 antigen bands were still detected by the positive culture supernatant when the oncosphere preparation was diluted ½ and ¼ and had approximate molecular weights of 22K and 35K (FIG. 10).

(2) When using the same positive liver culture supernatant to probe the Western blots of bladderwall (B) or scolex (S) preparations, the 2 oncosphere antigen bands were not detected (FIG. 10). This indicates that the 2 antigen bands specifically detected in the oncosphere preparation are stage specific for the oncosphere, the parasite stage most likely to be susceptible to immune attack.

(3) The 2 antigen bands detected when positive liver culture supernatant was used to "probe" the oncosphere Western blots were not detected when serum taken from the same sheep at the same time after infection was used as a probe (FIG. 11).

(4) The 2 oncospheral antigen bands were also detected when using culture supernatant from leukocytes isolated from the lymph nodes of recently infected animals (FIG. 12).

EXAMPLE 4

Corynebacterium pseudotuberculosis

*Caseous lymphadenitis* (abbrev. CLA, also called Cheesy Gland) is a chronic infection of sheep and goats that is caused by the bacterium *Corynebacterium pseudotuberculosis* (syn. *C. ovis*). A complex cell-free vaccine for CLA (GLANVAC, Commonwealth Serum Laboratories) is known in the prior art and is currently administered either alone or as part of a 6 component antibacterial vaccine (6 in 1). The protection afforded by this vaccine is attributed to the inactivated toxin (i.e. toxoid) component. The toxin has a relative molecular weight of approximately 31 k daltons when run on 12.5% SDS-PAGE under reducing conditions. Whilst this prior art vaccine does generate some protective effect, the vaccine is complex and expensive, and significant numbers of infections may still occur.

This example describes the isolation of a protective antigen from *Corynebacterium pseudotuberculosis* infections, being approximate molecular weight of 38–40 kilodaltons.

Identification of Antigen

Culture supernatants were obtained using essentially the same methods as described for *Haemonchus contortus* (Example 1). Challenge infections of immune and naive sheep were localized to the lower leg by injection of a suspension of viable *C. pseudotuberculosis* and the popliteal lymph node was taken and set up in culture 5 to 7 days later.

Western blot analysis of whole cells using culture supernatants showed:

(i) immune sheep recognized a complex pattern of antigens, but in the majority of animals the 38–40 kilodalton antigen was immunodominant (ii) naive (non-immune) animals strongly recognized the 38–40 kilodalton antigen and usually showed little other reactivity.

Extraction of Antigen

Confluent growth of *C. pseudotuberculosis* is obtained on Brian Hearth Infusion Agar by aerobic incubation at 37° C. for between 1 and 3 days. Cells are obtained by scraping from the solid medium.

The bacterial mass is resuspended in sterile water and washed by vortexing, then centrifugated at 3000×g for 15 min. The supernatant is decanted and the wet cell pellet extracted by resuspension in approximately 4 times its volume of a solution of 1.0% (w/v) sodium dodecyl sulphate (SDS) in water and heating to between 70° C.–100° C. for 10 minutes. Cells and debris are removed by centrifugation at 10,000 g. for 15 minutes. The crude mixture contains antigens other than that claimed.

The protein antigen can be purified from the complex mixture extracted with SDS from whole cells of *C. pseudotuberculosis*, as described above, or from cell-free culture supernatant. Conventional biochemical techniques can be used including ion exchange and molecular-sieve chromatography, ammonium sulphate fractionation together with hydrophobic chromatography. In addition, affinity chromatography can be used employing antibody isolated from the probe, immobilized on a suitable solid phase. Alternatively, polyclonal or monoclonal antibodies can be raised by immunization of animals with purified antigen.

The antigen remains soluble in ammonium sulphate solutions up to 50% saturation.

Characterization of 38–40 kD Antigen

The protein has an apparent molecular weight of between 38–40 kilodaltons when run under reducing conditions on a 12.5% SDS-polyacrylamide gel. It can be stained with Coomassie brilliant blue R250 and by silver stain. An amido black stain on nitrocellulose after Western blotting may also be used. Results are illustrated in FIG. 13, strip A.

Thin layer isoelectric focusing in 0.95% agarose containing 11.4% sorbitol and pH 5–8 ampholines localizes the antigen to a pI 6.8–6.9 using the following Biorad IEF markers (see FIG. 14): phycocyanin—4.65, B-lactoglobulin B-5.10, bovine carbonic anhydrase 6.0, human carbonic anhydrase 6.5, equine myoglobin 7.0, human hemoglobin A 7.1, human hemoglobin C 7.5, cytochrome C 9.6.

Amino-acid sequence analysis of the native antigen that had been eluted from a SDS-polyacrylamide gel reveals a portion of the sequence at or near the amino terminus to be (progressing toward the carboxy terminus):

E S A T L S K E P L K A S P G R A D T, V G V Q (or if preferred Glu, Ser, Ala, Thr, Leu, Ser, Lys, Glu, Pro, Leu, Lys, Ala, Ser, Pro, Gly, Arg, Ala, Asp, Thr, Val, Gly, Val, Gln (SEQ ID NO:1).

Finally, it is to be understood that various other modifications and/or alterations may be made without departing from the spirit of the present invention as outlined herein.

EXAMPLE 5

*Haemonchus contortus*

A larvae-specific surface antigen has previously been identified. This antigen is now further characterized and tested in protection trials.

Larval Exsheathment and Antigen Extraction

1. Spin down the larvae in 50 ml tubes (1–2 million larvae per tube). Draw off the liquid and discard. Resuspend the larvae in 5 ml of 160 mM NaCl, 87 mM NaHCO$_3$ in water.

2. Gas the larvae with 100% CO$_2$ for 3 minutes by bubbling gas through the liquid.

3. Close the tubes and incubate at 37° C. for 3 hrs.
4. If the larvae have satisfactorily exsheathed, transfer to 1.5 ml eppendorf tubes and spin down the larvae in the eppendorf centrifuge at full speed.
5. Resuspend the larvae by adding 1 ml 100 mM NaCl, 10 mM Tris HCl pH 7.4 (Tris buffer).
6. Place the tubes in a boiling water bath for 3 mins. Spin down the larvae and transfer the fluid to a clean tube.
7. Add a further 0.5 ml of Tris buffer, vortex, spin down and add the fluid to the first extract (surface extract).
8. Concentrate the extracts in a centricon 30. Reduce the volume to ca 500 µl. Wash with 1–2 ml Tris buffer.

The extract produced in this way is light yellow in color and the antigen is normally visible on SDS PAGE followed by coomassie blue staining.

Size Exclusion Chromatography

The antigen was further purified from extract prepared using the above protocol by size exclusion chromatography (see FIG. 15). The same buffer as that used for the extraction was used as the running buffer, in order not to subject the antigen to denaturing conditions. This step removed low molecular weight contaminants, resulting in a preparation that only shows a single major band by SDS PAGE (see FIG. 15B). This purified preparation was used for trial three, four and five and for further protein characterization work.

Lectin Screening

The antigen stains as a broad region between 60 and 90 kd on either an SDS PAGE or western blot, i.e. it does not form a sharply focused band. As one of the likely causes of this phenomenon is glycosylation, the purified antigen was screened with a set of biotinylated-lectins. The results showed that the antigen binds to wheat-germ agglutinin (WGA) and this was confirmed by WGA affinity chromatography (not shown). These results demonstrate and confirm that the antigen is glycosylated.

Protein Sequencing

The purified antigen did not yield N-terminal sequence data by Edman degradation. The N-terminus of the protein is probably blocked. Therefore the molecule was subjected to proteolytic digestion and peptide fragments isolated.

(i) Trypsin Digestion

Several enzymes were tested and the digestion monitored by western blot. Treatment with porcine trypsin resulted in the best digestion of the antigen i.e. no whole molecule visible on the western blot.

(ii) Purification of Peptides by HPLC

Peptides were purified by reversed phase microbore HPLC, buffer A was 5 mM ammonium acetate pH 6.8 and buffer B 90% acetonitrile in water. FIG. 16 is a typical HPLC profile.

(iii) Peptide Sequence Data

Two peptide sequences have been obtained:
(a) ILPATLNSQFIQA or Ile Leu Pro Ala Thr Leu Asn Ser Gln Phe Ile Gln Ala (SEQ ID NO:2); and
(b) ELVALSNSITAQQMAMMAZASPA or Glu Leu Val Ala Leu Ser Asn Ser Ile Thr Ala Gln Gln Met Ala Met Met Ata Xxx Ala Ser Pro Ala (SEQ ID NO:3).

Peptide (b) reacts strongly with a polyclonal serum raised against the native antigen in rabbits. Searches by computer of the protein and DNA databanks revealed no clear homology to any other molecules.

Vaccination Trials (i) Vaccination Trial One

A small immunization trial was conducted using the antigen on ground up nitrocellulose obtained from the immuno-reactive region after Western blotting (2 sheep). Two control sheep received a non-reactive region on the western blot. The primary immunization was given intra-abomasally, while subsequent immunization was administered subcutaneously in Freunds incomplete adjuvant. Two weeks after the second immunization the 4 sheep were challenged with 10,000 3rd stage H. contortus larvae and faecal egg counts monitored 20 days post the challenge infection.

Results of Trial One

The two vaccinated animals had lower egg counts than the controls. When egg counts of all the animals had fallen to very low levels the sheep were rechallenged. There was a subsequent delay in egg output in the vaccinated sheep by 2 weeks compared to the controls with one of the vaccinated sheep returning very low egg counts over the whole period. The results are shown in FIG. 17.

(ii) Vaccination Trial Two

A second trial was conducted with the whole surface extract using Freunds adjuvant, however, this time the sheep were vaccinated intramuscularly and subcutaneously.

Results of Trial Two

After a first challenge infection, no significant difference was found between the mean egg counts of the vaccinates and controls (FIG. 18). A local abomasal response was stimulated by giving both vaccinates and control sheep an abbreviated infection which was cured after 11 days by drenching with an anthelmintic. A second challenge infection was given and this immunization regime resulted in 7 of nine vaccinated sheep showing clear protection against the second challenge infection (FIG. 18). This result led to the emphasis being placed on intra-abomasal vaccination for the third trial in an attempt to direct the immune response to this site.

(iii) Vaccination Trial Three

The antigen used in this trial was a surface extract further purified by size exclusion chromatography (see FIG. 15).

Fourteen sheep were randomly divided into 2 groups; 7 received antigen (vaccinates) and 7 were PBS controls. The vaccination procedure is summarized in Table 1. Approximately 10 µg of protein was administered to each of the +ve sheep at each of the 3 vaccinations. This was mixed 5:1 with the adjuvant Alhydrogel, and held overnight at 4° C. Two sheep from each group received 10,000 U of recombinant ovine IL-1 which was incorporated into the adjuvant of the first vaccination only.

The first vaccination was given peripherally at 4 sites; 2 subcutaneously over the ribs on each side and 2 intramuscularly in the rump. The second and third vaccinations were given at 6 sites into the wall of the abomasum with the sheep under general anaesthetic and were given at 2 and 2.5 week intervals, respectively.

One of the IL-1 sheep died while under the general anaesthetic of the third vaccination.

Three and a half weeks after the final vaccination a challenge infection of 10,000 third-stage larvae, was orally administered, and 20 days following this, faecal samples were collected 3 times a week from each sheep and the eggs per gram (epg) of faeces were counted.

TABLE 1

Summary of the vaccination protocol.

| Week | No. of Sheep | Dose | Trtmt. | Site |
|---|---|---|---|---|
| 0 | 5 +ve | 10 μg antigen | 1st vacc | Peripheral |
| 0 | 2 +ve | 10 μg antigen + IL-1 | 1st vacc | Peripheral |
| 0 | 5 -ve | PBS | 1st vacc | Peripheral |
| 0 | 2 -ve | PBS + IL-1 | 1st vacc | Peripheral |
| 2 | 7 +ve | 10 μg antigen | 2nd vacc | Abomasal |
| 2 | 7 -ve | PBS | 2nd vacc | Abomasal |
| 4.5 | 7 +ve | 10 μg antigen | 3rd vacc | Abomasal |
| 4.5 | 7 -ve | PBS | 3rd vacc | Abomasal |
| 8 | All | 1 × 10⁴ larvae | Challenge | Oral |

Results of Trial Three

The overall infection rate at challenge was low even in control sheep. The reason for this may have been that the sheep were resistant to infection due to their age or the more likely cause was the inflammation caused by the intra-abomasal vaccination procedure.

The results show (FIG. 19) that vaccinated sheep had consistently lower faecal egg counts than the control animals, indicating that the antigen induced protection against Haemonchus infection.

(iv) Vaccination Trial Four

In this trial purified antigen was delivered by peripheral immunization only. Ten control and ten experimental sheep were given either PBS in Al(OH) or 10 μg antigen in Al(OH), respectively, 3 times by intradermal injections. All sheep were challenged with 10,000 L3 four weeks after the final vaccination.

Results of Trial Four

The group given antigen intradermally in alhydrogel (vaccinates) had significantly (P<0.05) lower faecal egg counts than the control group (FIG. 20a) indicating that a protective response had been produced against the parasite.

(v) Vaccination Trial Five

Figure 20A:
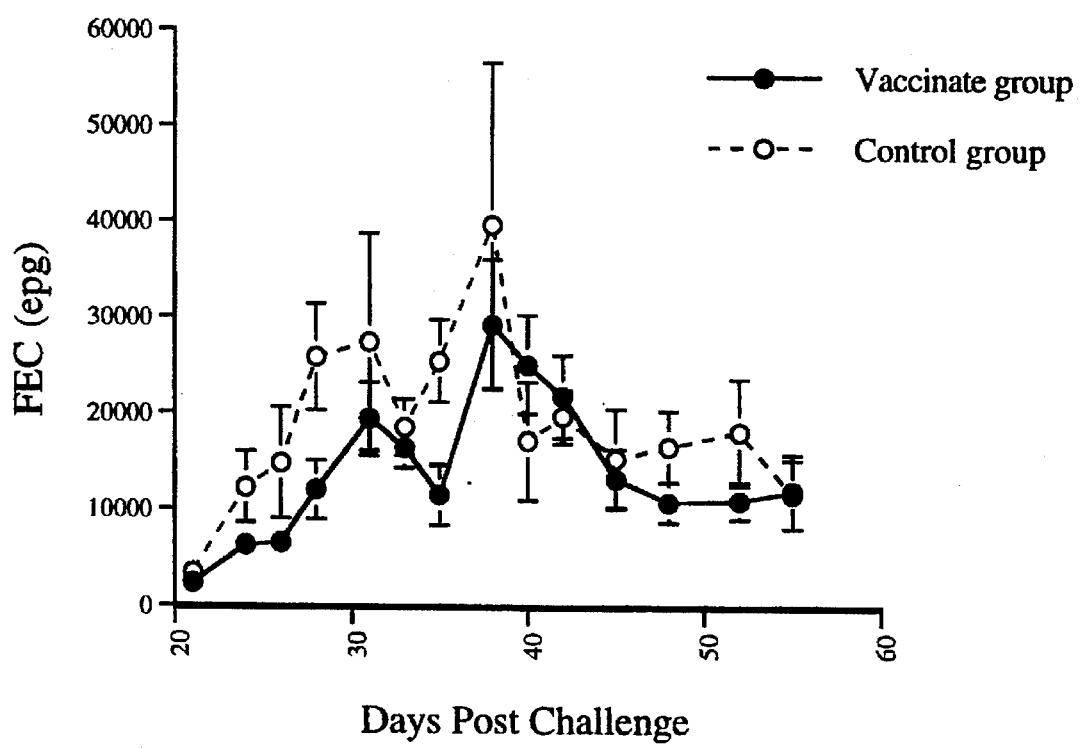
Figure 20B:
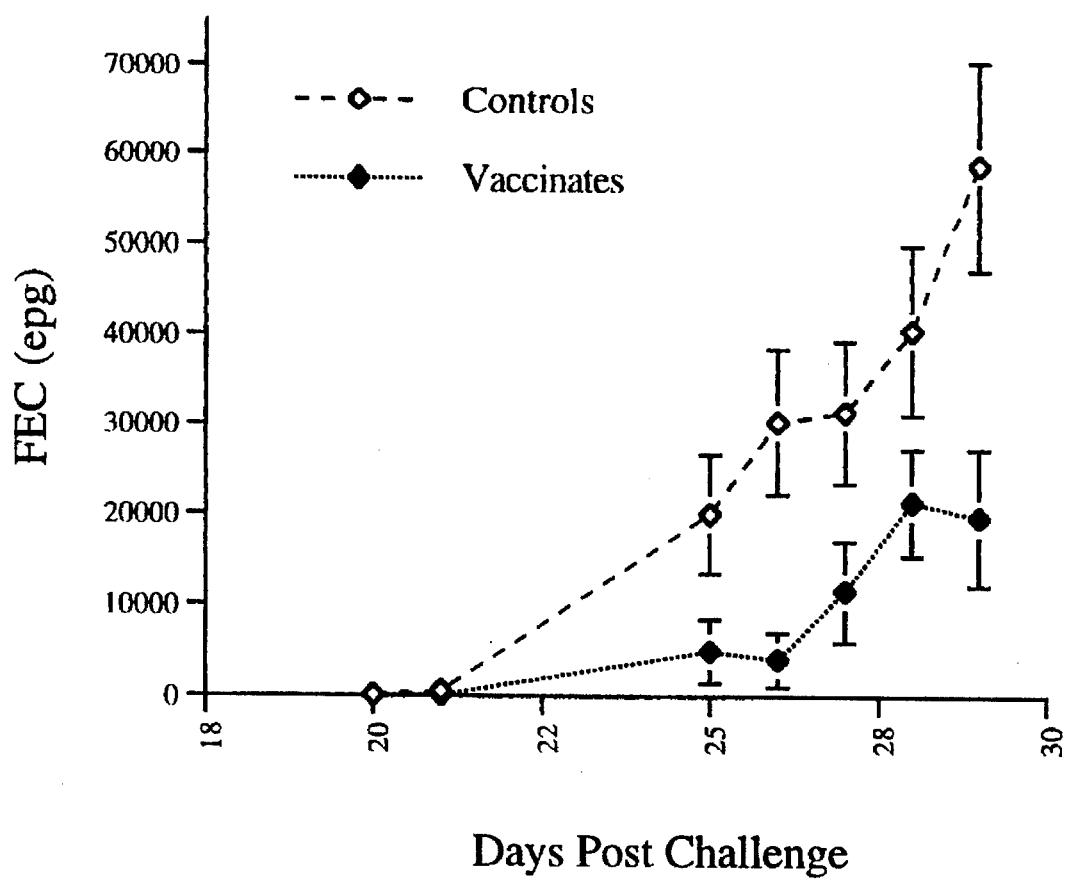

Six sheep were injected 3 times intradermally with approx. 17 μg purified *H. contortus* antigen in PBS with Al(OH). Five control sheep were injected similarly with Al(OH) and PBS only. All sheep were infected with 10,000 L3 larvae 15 days after the last immunization. Faecal egg counts were monitored until day 29 after infection and total worm counts in the abomasum were measured after post morten on days 32–33 after infection. Highly significant reductions in faecal egg counts were observed in the vaccinated groups compared to the controls (FIG. 20b). The worm burden in the vaccinated group was reduced by 42% compared to the control (1327 vs. 2352).

EXAMPLE 6

*Corynebacterium pseudotuberculosis*

Protein Purification

The 40 kD protein was partially purified by a 50% $(NH_4)_2SO_4$ cut in which it remained soluble, followed by hydrophobic column chromatography with an $(NH_4)_2SO_4$ gradient. The semi-purified protein was run in a preparative fashion on a 12.5% SDS polyacrylamide gel and the 40 kD protein was electroeluted in a 50 mM $(NH_4)_2CO_3$ buffer. Purified protein was cyanogen bromide digested and the resultant peptides were run on a step gradient polyacrylamide gel and electroblotted onto a PVDF sequencing grade membrane. Both the undigested 40 kD protein and the peptides were subject to N-terminal amino acid sequencing. This revealed the following amino acid sequences:

N-terminus
QSATLSKEPKLASPGRANRANTV+VQY (SEQ ID NO:4)

peptide 1:
VPLAHAEESKKPADL (SEQ ID NO:5)

peptide 2:
XSLFQVEDNQKSSQQXGX (SEQ ID NO:6)

peptide 3:
GPFAPANEGKFPDNEG (SEQ ID NO:7)

Cloning Strategy: The gene for the 40 kD protein was cloned from a size selected genomic DNA library from *C. pseudotuberculosis*. The library was screened with a PCR probe generated using oligonucleotide primers based on the amino acid sequence data.

Polymerase Chain Reaction (PCR)

Using the amino acid sequence data from both the N-terminus and the peptides, oligonucleotides were designed for use in PCR. In positions of high redundancy where any of the 4 bases could be encoded, sometimes inosine was used in an effort to decrease the redundancy of the oligonucleotide. The oligonucleotides from the peptides were designed to be complementary to the strand of DNA to that which is used for the N-terminally derived oligonucleotides. The following oligonucleotides were synthesized:

derived from N-terminus amino acid data:

5' AA(A,G)GA(A,G)CCITTIAA(A,G)GCITC(A,C,G,T)CCIGG 3' (SEQ ID NO:8)

5' AA(A,G)GA(A,G)CCITTIAA(A,G)GCIAG(C,T)CCIGG 3' (SEQ ID NO:9)

derived from peptide 1 amino acid data:

5' GCIGG(T,C)TT(T,C)TTIGA(T,C)TC(T,C)TCIGC(A,G)TG 3' (SEQ ID NO:10)

5' GCIGG(T,C)TT(T,C)TT(A,G)CT(T,C)TC(T,C)TCIGC(A,G)TG 3' (SEQ ID NO:11)

derived from peptide 3 amino acid data:

5' TTICC(T,C)TC(A,G)TTICGIGGIGC(ACGT)(A,T)(A,T)IGG 3' (SEQ ID NO:12)

The PCR reactions were performed in a programmable waterbath machine (Bartelt) with 30–60 cycles (92° C. 1 min., 50°–60° C. for 1 min., 72° C. for 1 min.) 100 ng of each oligonucleotide, in different combinations, and 10 ng of *C. pseudotuberculosis* genomic DNA was used for each reaction. The PCR products derived from these reactions were cloned into a dideoxy-thymidine vector. The cloned PCR products were nucleotide sequenced and compared with the nucleotide sequence predicted from the amino acid data. A 600 bp polynucleotide was found to have the predicted sequence.

Library Construction

*C. pseudotuberculosis* genomic DNA was extracted using phenol/chloroform followed by a cesium chloride density gradient. The DNA was digested with different rare cutting restriction enzymes, southern blotted and probed with the 600 bp PCR product. Using this information a size selected *C. pseudotuberculosis* genomic DNA library was constructed. DNA is digested with either the Xba1 or Cla1, run on a 0.8% agarose gel and the fragments which lay between 2–4 kbp are extracted from the agarose. This DNA was used in a ligation reaction with either Xba1 or Cla1 digested pBluescript SK-(Promega) and colonies were screened with the 600 bp polynucleotide PCR probe. Positive clones were isolated and digested with the appropriate endonuclease. The plasmids were found to contain a 2.6 kbp fragment for Xba1 and a 2.0 kbp fragment for Cla1 and the sizes were identical to that found by genomic DNA southern blot analysis. The clones were then restriction mapped with various 6 base cutting enzymes. The results of this are shown in FIG. 21.

Nucleotide Sequencing The positive clones were nucleotide sequenced using the Sanger dideoxy chain termination method and the results of this are shown in FIGS. 22A and 22B. An open reading frame of 1137 base pairs was found encoding a protein of 379 amino acids which corresponds to a molecular weight of 42909 daltons (FIGS. 22A and 22B). A predicted leader sequence of 31 amino acids with typical characteristics, as for other Gram positive leader sequences being hydrophobic and having an ala,x,ala cleavage site at the C-terminus of the leader sequence as shown. The N-terminal amino acid sequence data begins immediately after the predicted C-terminus of the leader sequence. The mature protein minus the leader sequence has a predicted molecular weight of 39,751 from 348 amino acids.

EXAMPLE 7

Southern Blot Analysis of Related Bacteria

Figure 23:
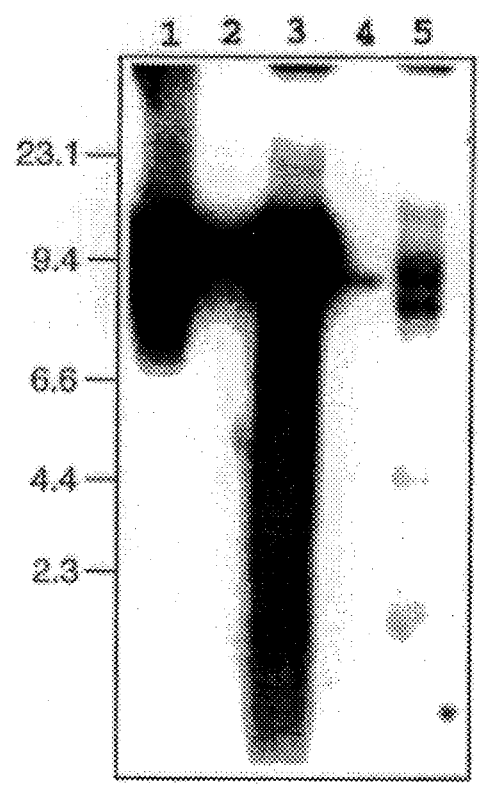

Genomic DNA from *Corynebacterium diptheriae intermedius, C. diptheriae gravis, Corynebacterium renale* and *Listeria monocytogenes* is digested with EcoR1 and southern blotted, probing with the open reading frame of the 40 KD gene. This showed that the gene encoding this protein has significant homology to genomic DNA from all of these bacterial species (FIG. 23).

Function of the 40 kDa Protein from *C. pseudotuberculosis*

The 40 kDa protein was shown in both native and recombinant form to have protease activity.

Protease activity was detected using gelatin substrate gels (FIG. 24). The use of class specific inhibitors (Table 2) has demonstrated that the 40 kDa proteolytic activity is of the serine class of proteases.

Vaccine Field Trial-II

A second vaccine field trial was designed and run to confirm the protective ability of the 40 kDa antigen against a *C. pseudotuberculosis* challenge, according the following schedule. 70, nine month old border leicester/merino cross sheep were divided into 3 groups:

1) control (25 sheep)

2) native 40 kDa (20 sheep)

3) Glanvac (25 sheep) (Commercial vaccine CSL Ltd.).

Vaccines for groups 1 and 2 were prepared by diluting the antigen in sterile PBS to the desired concentration, adding 1.1 ml of ISA-50 adjuvant (Seppic, France) to 1.0 ml to the aqueous phase and homogenizing by sonication, on ice, using an Edward's tapered probe at a power level of 3 for 6×10 secs. Sheep in group 2 received 100 μg of native 40 kDa as assessed by SDS-PAGE. Group 3 animals were immunized with the commercial vaccine Glanvac (CSL Ltd.) according to the manufacturer's instructions. Animals were vaccinated twice with a 3 week interval between vaccinations.

Challenge

Caseous material was obtained from an abattoir from sheep lymph nodes naturally infected with *C. pseudotuberculosis*, diluted with sterile PBS homogenized, aliquoted and snap frozen in liquid nitrogen. The *C. pseudotuberculosis* purity and concentration of this preparation was assessed by thawing out an aliquot, and plating a known amount in serial dilutions onto brain heart infusion plates. The bacterial count was $1 \times 10^7$ bacteria/g challenge material. Animals were challenged 14 days post secondary vaccination with *C. pseudotuberculosis* at sites by slicing the skin at the left and right prescapular and on the posterior aspect of both flanks with a scalpel blade and pasting approx. 5 g of the challenge material, per site.

Scoring of Infection

Animals were sacrificed 3 months post challenge at a commercial abattoir and lung and body lesions were tallied. It was noted that 17 animals had lost both ear tags; 2 from group 1, 9 from group 2, and 6 from group 3. Carcass and lung lesions (following removal and palpitation) were scored by frequency (Table 3) and size. A high infectivity rate of 91% was seen in control animals with 78% having carcass and 61% lung lesions. Significant levels of protection were seen in animals vaccinated with native 40 kDa and Glanvac with infection levels of 27% and 15% respectively. The mean lung lesion scores for the vaccinated sheep were significantly different from the scores of the control sheep, with scores at least 20 fold higher in the control group compared with the native 40 kDa and Glanvac vaccinates. There was no difference between the lung lesion scores of the two vaccinated groups. Significant differences were noted in the mean carcass lesion scores in animals from the two groups with significant protection, compared with animals in the control group.

In summary, this second field trial has shown that the purified 40 kDa native antigen from *C. pseudotuberculosis* is as protective as the current commercial vaccine which is based on a crude culture supernatant.

TABLE 2

Determination of the proteolytic class of the 40kD protease using specific inhibitors on samples run on 0.1% gelatin substrate gels.

| INHIBITOR | CLASS INHIBITED | 40KD PROTEASE ACTIVITY |
|---|---|---|
| pefa-block | serine | − |
| E64 | aspartic | +++ |
| pepstatin | aspartic | +++ |
| 1,10 phenanthroline | metallo | +++ |
| PMSF | serine | + |
| none | — | +++ |

TABLE 3

Results of the field trial showing mean infectivity rate of animals from each vaccinate group. Results are given for both carcass and lung lesions as the number of infected animals and the mean lesion score for each group.

| GROUP | TOTAL INFECTIONS | CARCASE LESIONS Infected/Total | Mean Lesion Score ± S.D. | LUNG LESIONS Infected/Total | Mean Lesion Score ± S.D. |
|---|---|---|---|---|---|
| 1. Control | 21/23 (91%) | 18/23 (78%) | 2.00 ± 1.53 | 14/23 (61%) | 7.35 ± 11.9 |
| 2. 40 kDa native | 3/11 (27%) | 2/11 (18%) | 0.73 ± 1.54 | 1/11 (9%) | 0.36 ± 1.15 |
| 3. Glanvac | 3/19 (15%) | 1/19 (5%) | 0.05 ± 0.22 | 2/10 (11%) | 0.32 ± 1.13 |

EXAMPLE 8

Protective Antigen(s) of Lucilia cuprina

The sheep blowfly, Lucilia cuprina, is the major ectoparasite of the Australian sheep industry. Flystrike is estimated to cost the Australian farming community in excess of 250 million dollars per annum. Flystrike causes a condition known as cutaneous myiasis, which refers to the growth and development of blowfly larvae on the skin of live sheep. Flystrike is estmated to kill approximately 3 million sheep in Australia each year. Current methods of control include crutching, mulesing, dipping and jetting using insecticides however increasing levels of resistance by the larvae to chemical agents and the animal welfare consideratons associated with mulesing have meant that other methods of control need to be sought. As a result of these problems, vaccination has been identified as an area worth pursuing.

Vaccine Trial 1

First instar L. cuprina antigens were identified using a modification of the method described herein above in order to protect sheep against flystrike.

The antigens were prepared by freeze-thawing the larvae twice in liquid nitrogen in a buffer containing 0.1M phosphate, 150 mM NaCl, 2 mM EDTA, 2 mM EGTA, 10 mM IAA and 1 mM DTT. This method removed mainly surface antigens from the larvae. The soluble fraction was passed down an immunoaffinity column prepared from antibodies isolated as described herein above. The antibodies were specifically prepared for flystrike. Specifically bound antigens were eluted using 3M NaSCN and the salt removed by washing with distilled water through an Amicon concentrator.

Prior to immunization, the 4 affinity isolated antigens were sonicated for 2 minutes on ice in Montanide ISA 25. Sheep were intradermally injected at two sites containing either Montanide and recombinant IL-1β (20 μg/site) plus antigen (20 μg/site), Montanide alone or saline on the same sheep (i.e. six sites per sheep). All sheep were vaccinated on three occasions at fortnightly intervals. Two weeks after the third vaccination the sheep were challenged on the same site as the intradermal injections with one hundred first instar larvae per site. After 48 hours the larvae were removed, counted and weighted (Table 4).

TABLE 4

The number of infections that became established between the vaccinated, adjuvant control and saline control treatments is presented in Table 4. The number of larvae recovered and their average larval weights are also given.

| | TREATMENT | | |
|---|---|---|---|
| | Vaccinated | Adjuvant Control | Saline Control |
| Number of Infections | 0/6 | 4/6 | 4/6 |
| Av. number of larvae recovered | 0 | 61 | 62 |
| Av. larval weights (mg) | 0 | 3.1 ± 1.7 | 3.4 ± 1.9 |

This experiement shows a highly protective local immune response was mediated using this combination of larval antigens and the vaccination regime described.

Vaccine Trial 2

In a second vaccination experiment the 4 antigens isolated from the first instar larvae were separated using a preparative isoelectric focusing apparatus (Bio-Rad). Four fractions were obtained which contained enriched amounts of the antigens identified by the AFC's as described herein above. The antigen fractions (20 pg/sheep/dose) were mixed with montanide ISA25 and recombinant IL-1β (rIL-1β) (60 pg rIL-1β per immunisation) sonicated as in Trial 1 and injected intradermally at two sites. One site containing montanide in saline acted as a control while a group of sheep received montanide plus rIL-1β (60 μg) only. Sheep were vaccinated two weeks apart for the first two vaccinations and then the third vaccination was given six weeks later. All sheep were challenged 3 weeks after the final vaccination. Two hundred first instar larvae were placed on each of the sites on each sheep and left for 48 hours. Protection was assessed by the number of successful infections (Table 5).

TABLE 5

This table shows the degree of protection that was achieved when sheep were vaccinated with the different larval antigens.

| Antigen number | No. of sheep per group | No. of infections per group | No. of successful larval infections | % protection |
|---|---|---|---|---|
| 1 | 4 | 12 | 7 | 42 |
| 2 | 4 | 12 | 7 | 42 |
| 3 | 3 | 9 | 1 | 88 |
| 4 | 4 | 12 | 10 | 17 |
| Control | 4 | 10 | 8 | 20 |

These results show that a significant degree of systemic protection in sheep was obtained with three of the four antigens, in particular, those antigens present in antigen group three were shown to be highly protective.

EXAMPLE 9

Protective Antigens of *Ostertagia circumcincta* (Small Brown Stomach Worm)

*O. circumcincta* is an intestinal nematode that parasitizes sheep. The 28–35 kD antigen was prepared by the general methods described above and administered to sheep. The effect of vaccination with this antigen was monitored by the quantity of parasite eggs observed in the sheep feces.

Antibody probes and antigens were produced by the method described in Example 4 for *C. pseudotuberculosis* antigens. The antibody probes identified five protein antigens that have molecular weights of 28–35 kD, as determined by SDS-PAGE analysis. These five antigens were prepared from the infectious third stage larvae (L3) of *O. circumcincta* by elution from polyacrylamide gels run in the presence of the cationic detergent cetyltrimethyl ammonium bromide.

These five protein antigens were combined into a single vaccine. Sheep were vaccinated on three occasions with 100 μg of antigen with an adjuvant of 600 μg Quill A (Superfos, Denmark) by intradermal injection. Control sheep received vehicle and adjuvant lacking antigenic peptide. Two weeks after the final vaccination, both control sheep and vaccinated sheep were challenged per os with 20,000 third stage larvae of *O. circumcincta*.

Two vaccine trials were run. Trial 1 included five vaccinated sheep and three control sheep. FIG. 25 shows the levels of eggs per gram of feces (epg) in vaccinated (solid line) and control (dashed line) sheep from days 16–31 after infection. Considering the vaccinated sheep as a group and the control sheep as a group, the vaccine reduced egg levels by approximately 75% at 30 and 31 days after vaccination. On each day the vaccinated sheep have lower levels of infection than control sheep.

In the second vaccine trial, there were ten vaccinated sheep and eight control sheep. FIG. 26 shows the levels of eggs per gram of feces (epg) in vaccinated (solid line) and control (dashed line) sheep from days 18–42 after infection. Most of the timepoints show reduced levels of eggs in feces for vaccinated sheep. In this trial peak egg levels were reduced by 65% for vaccinated sheep compared to control sheep.

References

Henderson, L. E., Oroszlan, S. and Konigsberg, W. 1979. *Analytical Biochemistry* 93: 153–157.

Kerlero de Rosbo, N., Carnegie, P. R., Bernard, C. C. A. and Linthicum, D. S. 1984. *Neurochemistry Research*, 9: 1359–1369.

Laemmli, U. K. 1970. Nature (London) 277: 680–685.

McLachlan, R., and Cornell, F. N. 1978. *Pathology*, 10: 395.

Morrissey, J. H. 1981. *Analytical Biochemistry*, 117: 307–310.

Ward, E. S. Gussow, D., Griffiths, A. D., Jones, P. T. and Winter, G. 1989, Nature 341: 544–546.

---

What is claimed is:

1. An antigen isolated from oncosphere stage of *Taenia hydatigena*, selected from the group consisting of antigens having a molecular weight of 25 and 34 kilodaltons as determined on SDS-PAGE.

2. An antigen, isolated from L₄ larvae stage of *Haemonchus contortus*, having a molecular weight of 67 to 75 kilodaltons as determined on SDS-PAGE, that provides protection for an animal against *Haemonchus contortus* infections.

3. An antigen, isolated from newly encysted juvenile stage of *Fasciola hepatica*, having a molecular weight of 120 to 125 kilodaltons as determined on SDS-PAGE.

4. An antigen, isolated from *Corynebacterium pseudotuberculosis*, having a molecular weight of 40 kilodaltons as determined on SDS-PAGE, that provides protection for an animal against *Corynebacterium pseudotuberculosis* infections.

5. An antigen, isolated from *Corynebacterium pseudotuberculosis*, having a molecular weight of 40 kilodaltons as determined on SDS-PAGE and having an NH₂ terminal sequence of GluSerAlaThrLeuSerLysGluProLeuLysAlaSerProGlyArgAlaAspThrValGlyValGln (SEQ ID NO: 1), that provides protection for an animal against *Corynebacterium pseudotuberculosis* infections.

* * * * *

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:1:

```
Glu  Ser  Ala  Thr  Leu  Ser  Lys  Glu  Pro  Leu  Lys  Ala  Ser  Pro  Gly  Arg
 1              5                           10                          15

Ala  Asp  Thr  Val  Gly  Val  Gln
                20
```

( 2 ) INFORMATION FOR SEQ ID NO:2:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear (i i) MOLECULE TYPE: peptide (i i i) HYPOTHETICAL: NO (i v) ANTI-SENSE: NO (v) FRAGMENT TYPE: internal (v i) ORIGINAL SOURCE:

(x i) SEQUENCE DESCRIPTION: SEQ ID NO:2:

Ile Leu Pro Ala Thr Leu Asn Ser Gln Phe Ile Gln Ala
 1               5                  10

(2) INFORMATION FOR SEQ ID NO:3:

(i) SEQUENCE CHARACTERISTICS:
        (A) LENGTH: 23 amino acids
        (B) TYPE: amino acid
        (C) STRANDEDNESS: single
        (D) TOPOLOGY: linear (i i) MOLECULE TYPE: peptide (i i i) HYPOTHETICAL: NO (i v) ANTI-SENSE: NO (v) FRAGMENT TYPE: internal (v i) ORIGINAL SOURCE:

(x i) SEQUENCE DESCRIPTION: SEQ ID NO:3:

Glu Leu Val Ala Leu Ser Asn Ser Ile Thr Ala Gln Gln Met Ala Met
 1               5                  10                  15

Met Ala Xaa Ala Ser Pro Ala
             20

(2) INFORMATION FOR SEQ ID NO:4:

(i) SEQUENCE CHARACTERISTICS:
        (A) LENGTH: 26 amino acids
        (B) TYPE: amino acid
        (C) STRANDEDNESS: single
        (D) TOPOLOGY: linear (i i) MOLECULE TYPE: peptide (i i i) HYPOTHETICAL: NO (i v) ANTI-SENSE: NO (v) FRAGMENT TYPE: internal (v i) ORIGINAL SOURCE:

(x i) SEQUENCE DESCRIPTION: SEQ ID NO:4:

Gln Ser Ala Thr Leu Ser Lys Glu Pro Lys Leu Ala Ser Pro Gly Arg
 1               5                  10                  15

Ala Asn Arg Ala Asn Thr Val Val Gln Tyr
             20                  25

(2) INFORMATION FOR SEQ ID NO:5:

(i) SEQUENCE CHARACTERISTICS:
        (A) LENGTH: 15 amino acids
        (B) TYPE: amino acid
        (C) STRANDEDNESS: single
        (D) TOPOLOGY: linear (i i) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:5:

| Val | Pro | Leu | Ala | His | Ala | Glu | Glu | Ser | Lys | Lys | Pro | Ala | Asp | Leu |
|---|---|---|---|---|---|---|---|---|---|---|---|---|---|---|
| 1 | | | | 5 | | | | | 10 | | | | | 15 |

(2) INFORMATION FOR SEQ ID NO:6:

(i) SEQUENCE CHARACTERISTICS:
(A) LENGTH: 18 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:6:

| Xaa | Ser | Leu | Phe | Gln | Val | Glu | Asp | Asn | Gln | Lys | Ser | Ser | Gln | Gln | Xaa |
|---|---|---|---|---|---|---|---|---|---|---|---|---|---|---|---|
| 1 | | | | 5 | | | | | 10 | | | | | 15 | |

Gly Xaa (2) INFORMATION FOR SEQ ID NO:7:

(i) SEQUENCE CHARACTERISTICS:
(A) LENGTH: 16 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:7:

| Gly | Pro | Phe | Ala | Pro | Ala | Asn | Glu | Gly | Lys | Phe | Pro | Asp | Asn | Glu | Gly |
|---|---|---|---|---|---|---|---|---|---|---|---|---|---|---|---|
| 1 | | | | 5 | | | | | 10 | | | | | 15 | |

(2) INFORMATION FOR SEQ ID NO:8:

(i) SEQUENCE CHARACTERISTICS:
(A) LENGTH: 26 base pairs
(B) TYPE: nucleic acid
(C) STRANDEDNESS: single
(D) TOPOLOGY: linear (ii) MOLECULE TYPE: Genomic DNA (iii) HYPOTHETICAL: NO (iv) ANTI-SENSE: NO (v) FRAGMENT TYPE:

( v i ) ORIGINAL SOURCE:

( i x ) FEATURE:
    ( A ) NAME/KEY: Other
    ( B ) LOCATION: 1...26
    ( D ) OTHER INFORMATION: NOTE=/POSITIONS 9, 12, 18
        AND 21 ARE ISOSINE ( x i ) SEQUENCE DESCRIPTION: SEQ ID NO:8:

AARGARCCNT TNAARGCNTC NCCNGG                    26

( 2 ) INFORMATION FOR SEQ ID NO:9:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: Genomic DNA ( i i i ) HYPOTHETICAL: NO ( i v ) ANTI-SENSE: NO ( v ) FRAGMENT TYPE:

( v i ) ORIGINAL SOURCE:

( i x ) FEATURE:
        ( A ) NAME/KEY: Other
        ( B ) LOCATION: 1...26
        ( D ) OTHER INFORMATION: NOTE=/POSITIONS 9, 12 AND
            18 ARE ISOSINE ( x i ) SEQUENCE DESCRIPTION: SEQ ID NO:9:

AARGARCCNT TNAARGCNAG YCCNGG                    26

( 2 ) INFORMATION FOR SEQ ID NO:10:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: Genomic DNA ( i i i ) HYPOTHETICAL: NO ( i v ) ANTI-SENSE: NO ( v ) FRAGMENT TYPE:

( v i ) ORIGINAL SOURCE:

( i x ) FEATURE:
        ( A ) NAME/KEY: Other
        ( B ) LOCATION: 1...26
        ( D ) OTHER INFORMATION: NOTE=/POSITIONS 3, 12 AND
            21 ARE ISOSINE ( x i ) SEQUENCE DESCRIPTION: SEQ ID NO:10:

GCNGG YTT Y T TNGA Y TC Y TC-
NGCRTG                                                                  26

( 2 ) INFORMATION FOR SEQ ID NO:11:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(ix) FEATURE:
  (A) NAME/KEY: Other
  (B) LOCATION: 1...26
  (D) OTHER INFORMATION: NOTE=/POSITIONS 3 AND 21 ARE
    ISOSINE (xi) SEQUENCE DESCRIPTION: SEQ ID NO:11:

```
GCNGG YTTYT TRCTY TCYTC NGCRTG                              26
```

(2) INFORMATION FOR SEQ ID NO:12:

(i) SEQUENCE CHARACTERISTICS:
  (A) LENGTH: 26 base pairs
  (B) TYPE: nucleic acid
  (C) STRANDEDNESS: single
  (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(ix) FEATURE:
  (A) NAME/KEY: Other
  (B) LOCATION: 1...26
  (D) OTHER INFORMATION: NOTE=/POSITIONS 3, 12, 15,
    18 AND 24 ARE ISOSINE (xi) SEQUENCE DESCRIPTION: SEQ ID NO:12:

```
TTNCC YTCRT TNCGN GGNGC NWWNGG                              26
```

(2) INFORMATION FOR SEQ ID NO:13:

(i) SEQUENCE CHARACTERISTICS:
  (A) LENGTH: 1140 base pairs
  (B) TYPE: nucleic acid
  (C) STRANDEDNESS: single
  (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:13:

```
ATGCATAATT  CTCCTCGATC  AGTCTCACGC  CTTATTACGG  TAGGCATAAC  TTCCGCTCTC   60
TTTGCTAGCA  CTTTTAGCGC  TGTAGCATCC  GCAGAGTCTG  CAACCTTGTC  CAAAGAGCCG  120
CTGAAAGCAA  GCCCTGGACG  CGCAGACACG  GTGGGAGTGC  AAACAACATG  TAACGCCAAA  180
CCAATTTTCT  TCGGCTATTA  CCGCACCTGG  CGCGATAAGG  CCATCCAGCT  TAAGGACGAC  240
GACCCTTGGA  AAGACAAGCT  CCAGGTCAAG  CTGACGGACA  TTCCCGAGCA  CGTCAATATG  300
```

```
GTCTCGTTGT  TCCATGTGGA  AGATAATCAG  AAGAGCGATC  AGCAATTCTG  GGAAACCTTC   360

CACAGGGAAT  ACCAGCCCGA  GCTCAAAAAA  CGCGGTACCC  GAGTTGTTCC  GACCGTCGGC   420

GCGCAGTTGC  TGCTCAATAA  GATTAAAGAT  AAAAACCTCT  ACGGAAAGCA  TGTTGAAGAC   480

GACTACAAGT  ATCGGGAGAT  AGCACGCGAT  GTATATAACG  AGTACGTCGT  CAAACATAAT   540

CTTGATGGCT  TAGACGTAGA  CATGGAACTC  CGCCAGGTGG  AGAAACAACT  AAACCTCAAG   600

TCGCAGCTGC  GCAAAATCAT  GGGAGCGTTC  TCCGAGCTCA  TGGGCCCCAA  AGCCCCTGCA   660

AATGAGGGGA  AAAAGCCAGA  TCATGAGGGT  TATAAGTACC  TTATTTATGA  CACCTTTGAT   720

AATGCCCAGA  CATCACAGGT  CGGGCTGGTC  GCAGACCTAG  TGGATTATGT  CCTGGCTCAG   780

ACCTATAAGA  AGGACACAAA  AGAGAGCGTC  ACCCAGGTAT  GGAATGGCTT  CCGAGACAAG   840

ATCAATTCCT  GCCAGTTTAT  GGCTGGGTAT  GCCCACCGGG  AGGAAAATGA  CACAAATCGA   900

TTCCTCACCG  CAGTAGGAGA  AGTGAATAAA  TCTGGCGCAA  TGCAGGTCGC  AGAGTGGAAG   960

CCAGAAGGCG  GAGAAAAGGG  CGGGACCTTC  GCCTACGCCC  TGGATAGGGA  CGGGCGCACC  1020

TACGATGGAG  ACGATTTCAC  CACACTCAAA  CCGACCGATT  TTGCCTTTAC  CAAGCGCGCA  1080

ATCGAGCTAA  CCACCGGGGA  ATCGTCTACA  GACTTAGGAA  AGCCAACTGG  TTCTAGATAA  1140
```